(12) United States Patent
Mason et al.

(10) Patent No.: US 11,963,842 B2
(45) Date of Patent: *Apr. 23, 2024

(54) APPLIANCES FOR INTRAORAL DELIVERY OF AGENTS

(71) Applicant: Align Technology, Inc., San Jose, CA (US)

(72) Inventors: David Mason, Morgan Hill, CA (US); Shiva Sambu, Milpitas, CA (US); Chunhua Li, Cupertino, CA (US); Yan Chen, Cupertino, CA (US)

(73) Assignee: Align Technology, Inc., San Jose, CA (US)

( * ) Notice: Subject to any disclaimer, the term of this patent is extended or adjusted under 35 U.S.C. 154(b) by 26 days.

This patent is subject to a terminal disclaimer.

(21) Appl. No.: 17/866,321

(22) Filed: Jul. 15, 2022

(65) Prior Publication Data

US 2023/0018058 A1 Jan. 19, 2023

Related U.S. Application Data

(63) Continuation of application No. 15/202,139, filed on Jul. 5, 2016, now Pat. No. 11,419,710.

(Continued)

(51) Int. Cl.
*A61C 19/06* (2006.01)
*A61C 7/00* (2006.01)
(Continued)

(52) U.S. Cl.
CPC ............ *A61C 19/066* (2013.01); *A61C 7/002* (2013.01); *A61C 7/08* (2013.01); *A61C 7/10* (2013.01);
(Continued)

(58) Field of Classification Search
CPC ..... A61C 19/02; A61C 19/063; A61C 19/066; A61C 7/002; A61C 7/008; A61C 7/10;
(Continued)

(56) References Cited

U.S. PATENT DOCUMENTS 5,820,368 A 10/1998 Wolk
6,386,864 B1 5/2002 Kuo
(Continued)

FOREIGN PATENT DOCUMENTS

WO 2021055164 A1 3/2021

OTHER PUBLICATIONS

Keating, S., et al., "Beyond 3D Printing: The New Dimensions of Additive Fabrication," Designing for Emerging Technologies: UX for Genomics, Robotics, and the Internet of Things, 2014, pp. 379-405.

(Continued)

*Primary Examiner* — Edward Moran
*Assistant Examiner* — Matthew P Saunders
(74) *Attorney, Agent, or Firm* — FORTEM IP LLP

(57) ABSTRACT

Appliances for intraoral delivery of agents are provided. In some embodiments, an appliance includes a shell having an inner surface and an outer surface, the inner surface defining a plurality of tooth-receiving cavities configured to apply a repositioning force to a patient's teeth, and the outer surface oriented away from the patient's teeth. The appliance can also include a reservoir integrally formed in the outer surface of the shell, the reservoir being configured to store at least one agent. The appliance can further include a membrane covering at least a portion of the reservoir to control release of the agent into an intraoral cavity of the patient. The membrane can include a plurality of pores that (Continued)

are configured to open based at least in part on a temperature of the patient's intraoral cavity to allow the at least one agent to pass therethrough.

10 Claims, 16 Drawing Sheets

Related U.S. Application Data

(60) Provisional application No. 62/189,303, filed on Jul. 7, 2015, provisional application No. 62/189,318, filed on Jul. 7, 2015.

(51) Int. Cl.
| | | |
|---|---|---|
| *A61C 7/08* | (2006.01) | |
| *A61C 7/10* | (2006.01) | |
| *A61C 13/00* | (2006.01) | |
| *B23K 26/362* | (2014.01) | |
| *B44C 1/22* | (2006.01) | |
| *B44C 1/28* | (2006.01) | |
| *G06Q 30/0601* | (2023.01) | |
| *G16H 30/20* | (2018.01) | |
| *A44C 15/00* | (2006.01) | |
| *B33Y 10/00* | (2015.01) | |
| *B33Y 30/00* | (2015.01) | |
| *B33Y 50/00* | (2015.01) | |
| *B33Y 80/00* | (2015.01) | |

(52) U.S. Cl.
CPC ...... *A61C 13/0013* (2013.01); *A61C 13/0019* (2013.01); *A61C 19/063* (2013.01); *B23K 26/362* (2013.01); *B44C 1/227* (2013.01); *B44C 1/228* (2013.01); *B44C 1/28* (2013.01); *G06Q 30/0621* (2013.01); *G06Q 30/0643* (2013.01); *G16H 30/20* (2018.01); *A44C 15/007* (2013.01); *B33Y 10/00* (2014.12); *B33Y 30/00* (2014.12); *B33Y 50/00* (2014.12); *B33Y 80/00* (2014.12)

(58) Field of Classification Search
CPC ............. A61C 13/0013; A61C 13/0019; A61J 7/0092; A44C 15/007
See application file for complete search history.

(56) References Cited

U.S. PATENT DOCUMENTS

| | | | |
|---|---|---|---|
| 6,450,807 B1 | 9/2002 | Chishti et al. | |
| 6,454,565 B2 | 9/2002 | Phan et al. | |
| 6,607,382 B1* | 8/2003 | Kuo ........................ A61P 1/02 433/80 | |
| 6,702,575 B2 | 3/2004 | Hilliard | |
| 6,783,604 B2 | 8/2004 | Tricca | |
| 6,790,035 B2 | 9/2004 | Tricca et al. | |
| 6,814,574 B2 | 11/2004 | Abolfathi et al. | |
| 6,830,450 B2 | 12/2004 | Knopp et al. | |
| 6,947,038 B1 | 9/2005 | Anh et al. | |
| 7,074,039 B2 | 7/2006 | Kopelman et al. | |
| 7,104,792 B2 | 9/2006 | Taub et al. | |
| 7,121,825 B2 | 10/2006 | Chishti et al. | |
| 7,160,107 B2 | 1/2007 | Kopelman et al. | |
| 7,192,273 B2 | 3/2007 | McSurdy, Jr. | |
| 7,347,688 B2 | 3/2008 | Kopelman et al. | |
| 7,448,514 B2 | 11/2008 | Wen | |
| 7,481,121 B1 | 1/2009 | Cao | |
| 7,543,511 B2 | 6/2009 | Kimura et al. | |
| 7,658,610 B2 | 2/2010 | Knopp | |
| 7,771,195 B2 | 8/2010 | Knopp et al. | |
| 7,871,269 B2 | 1/2011 | Wu et al. | |
| 7,878,805 B2 | 2/2011 | Moss et al. | |
| 7,883,334 B2 | 2/2011 | Li et al. | |
| 7,914,283 B2 | 3/2011 | Kuo | |
| 8,152,518 B2 | 4/2012 | Kuo | |
| 8,172,569 B2 | 5/2012 | Matty et al. | |
| 8,235,715 B2 | 8/2012 | Kuo | |
| 8,292,617 B2 | 10/2012 | Brandt et al. | |
| 8,337,199 B2 | 12/2012 | Wen | |
| 8,401,686 B2 | 3/2013 | Moss et al. | |
| 8,517,726 B2 | 8/2013 | Kakavand et al. | |
| 8,562,337 B2 | 10/2013 | Kuo et al. | |
| 8,641,414 B2 | 2/2014 | Borovinskih et al. | |
| 8,684,729 B2 | 4/2014 | Wen | |
| 8,708,697 B2 | 4/2014 | Li et al. | |
| 8,771,149 B2 | 7/2014 | Rahman et al. | |
| 8,899,977 B2 | 12/2014 | Cao et al. | |
| 8,936,463 B2 | 1/2015 | Mason et al. | |
| 8,936,464 B2 | 1/2015 | Kopelman | |
| 9,022,781 B2 | 5/2015 | Kuo et al. | |
| 9,119,691 B2 | 9/2015 | Namiranian et al. | |
| 9,241,774 B2 | 1/2016 | Li et al. | |
| 9,326,831 B2 | 5/2016 | Cheang | |
| 9,433,476 B2 | 9/2016 | Khardekar et al. | |
| 9,655,691 B2 | 5/2017 | Li et al. | |
| 9,675,427 B2 | 6/2017 | Kopelman | |
| 9,700,385 B2 | 7/2017 | Webber | |
| 9,744,001 B2 | 8/2017 | Choi et al. | |
| 9,844,424 B2 | 12/2017 | Wu et al. | |
| 10,045,835 B2 | 8/2018 | Boronkay et al. | |
| 10,111,730 B2 | 10/2018 | Webber et al. | |
| 10,150,244 B2 | 12/2018 | Sato et al. | |
| 10,201,409 B2* | 2/2019 | Mason ....................... B44C 1/28 | |
| 10,213,277 B2 | 2/2019 | Webber et al. | |
| 10,299,894 B2 | 5/2019 | Tanugula et al. | |
| 10,363,116 B2 | 7/2019 | Boronkay | |
| 10,383,705 B2 | 8/2019 | Shanjani et al. | |
| D865,180 S | 10/2019 | Bauer et al. | |
| 10,449,016 B2 | 10/2019 | Kimura et al. | |
| 10,463,452 B2 | 11/2019 | Matov et al. | |
| 10,470,847 B2 | 11/2019 | Shanjani et al. | |
| 10,492,888 B2 | 12/2019 | Chen et al. | |
| 10,517,701 B2 | 12/2019 | Boronkay | |
| 10,537,406 B2 | 1/2020 | Wu et al. | |
| 10,537,463 B2 | 1/2020 | Kopelman | |
| 10,548,700 B2 | 2/2020 | Fernie | |
| 10,555,792 B2 | 2/2020 | Kopelman et al. | |
| 10,588,776 B2 | 3/2020 | Cam et al. | |
| 10,613,515 B2 | 4/2020 | Cramer et al. | |
| 10,639,134 B2 | 5/2020 | Shanjani et al. | |
| 10,743,964 B2 | 8/2020 | Wu et al. | |
| 10,758,323 B2 | 9/2020 | Kopelman | |
| 10,781,274 B2 | 9/2020 | Liska et al. | |
| 10,813,720 B2 | 10/2020 | Grove et al. | |
| 10,874,483 B2 | 12/2020 | Boronkay | |
| 10,881,487 B2 | 1/2021 | Cam et al. | |
| 10,912,629 B2 | 2/2021 | Tanugula et al. | |
| 10,959,810 B2 | 3/2021 | Li et al. | |
| 10,993,783 B2 | 5/2021 | Wu et al. | |
| 11,026,831 B2 | 6/2021 | Kuo | |
| 11,045,282 B2 | 6/2021 | Kopelman et al. | |
| 11,045,283 B2 | 6/2021 | Riley et al. | |
| 11,103,330 B2 | 8/2021 | Webber et al. | |
| 11,123,156 B2 | 9/2021 | Cam et al. | |
| 11,154,382 B2 | 10/2021 | Kopelman et al. | |
| 11,166,788 B2 | 11/2021 | Webber | |
| 11,174,338 B2 | 11/2021 | Liska et al. | |
| 11,219,506 B2 | 1/2022 | Shanjani et al. | |
| 11,259,896 B2 | 3/2022 | Matov et al. | |
| 11,273,011 B2 | 3/2022 | Shanjani et al. | |
| 11,278,375 B2 | 3/2022 | Wang et al. | |
| 11,318,667 B2 | 5/2022 | Mojdeh et al. | |
| 11,331,166 B2 | 5/2022 | Morton et al. | |
| 11,344,385 B2 | 5/2022 | Morton et al. | |
| 11,376,101 B2 | 7/2022 | Sato et al. | |
| 11,419,702 B2 | 8/2022 | Sato et al. | |
| 11,419,710 B2* | 8/2022 | Mason ................. B23K 26/362 | |
| 2002/0192617 A1 | 12/2002 | Phan et al. | |
| 2004/0115587 A1 | 6/2004 | Breining et al. | |
| 2004/0166462 A1 | 8/2004 | Phan et al. | |
| 2004/0166463 A1 | 8/2004 | Wen et al. | |

(56) References Cited

U.S. PATENT DOCUMENTS

| | | |
|---|---|---|
| 2005/0014105 A1 | 1/2005 | Abolfathi et al. |
| 2005/0186524 A1 | 8/2005 | Abolfathi et al. |
| 2005/0244768 A1 | 11/2005 | Taub et al. |
| 2006/0019218 A1 | 1/2006 | Kuo |
| 2006/0078841 A1 | 4/2006 | DeSimone et al. |
| 2006/0115782 A1 | 6/2006 | Li et al. |
| 2006/0115785 A1* | 6/2006 | Li ............... A61P 29/00 433/80 |
| 2006/0116561 A1* | 6/2006 | Tricca ........... A61B 5/0088 600/309 |
| 2006/0199142 A1 | 9/2006 | Liu et al. |
| 2006/0234179 A1 | 10/2006 | Wen et al. |
| 2008/0118882 A1* | 5/2008 | Su .............. A61K 6/30 523/105 |
| 2008/0119698 A1* | 5/2008 | Tricca ........... A61B 5/682 600/309 |
| 2008/0160473 A1 | 7/2008 | Li et al. |
| 2008/0182218 A1* | 7/2008 | Chen ............ A61C 19/063 433/80 |
| 2008/0286716 A1 | 11/2008 | Sherwood |
| 2008/0286717 A1 | 11/2008 | Sherwood |
| 2008/0318178 A1* | 12/2008 | Abolfathi ......... A61C 7/00 433/6 |
| 2009/0117507 A1* | 5/2009 | Abolfathi ......... A61C 7/00 433/80 |
| 2009/0280450 A1 | 11/2009 | Kuo |
| 2010/0055635 A1 | 3/2010 | Kakavand |
| 2010/0129763 A1 | 5/2010 | Kuo |
| 2011/0269092 A1 | 11/2011 | Kuo et al. |
| 2012/0261847 A1 | 10/2012 | Sirovskiy et al. |
| 2013/0122448 A1 | 5/2013 | Kitching |
| 2014/0061974 A1 | 3/2014 | Tyler |
| 2014/0067334 A1 | 3/2014 | Kuo |
| 2014/0072926 A1 | 3/2014 | Valoir |
| 2014/0265034 A1 | 9/2014 | Dudley |
| 2015/0102532 A1 | 4/2015 | DeSimone et al. |
| 2015/0265376 A1 | 9/2015 | Kopelman |
| 2015/0366638 A1 | 12/2015 | Kopelman et al. |
| 2016/0193014 A1 | 7/2016 | Morton et al. |
| 2016/0256240 A1 | 9/2016 | Shivapuja et al. |
| 2016/0278899 A1* | 9/2016 | Heller ............ A61K 9/0053 |
| 2017/0007359 A1 | 1/2017 | Kopelman et al. |
| 2017/0007360 A1 | 1/2017 | Kopelman et al. |
| 2017/0007361 A1 | 1/2017 | Boronkay et al. |
| 2017/0007366 A1 | 1/2017 | Kopelman et al. |
| 2017/0008333 A1* | 1/2017 | Mason ............ B44C 1/228 |
| 2017/0135792 A1 | 5/2017 | Webber |
| 2017/0135793 A1 | 5/2017 | Webber et al. |
| 2017/0165032 A1 | 6/2017 | Webber et al. |
| 2018/0271620 A1 | 9/2018 | Rodriguez et al. |
| 2018/0360567 A1 | 12/2018 | Xue et al. |
| 2019/0000592 A1 | 1/2019 | Cam et al. |
| 2019/0000593 A1 | 1/2019 | Cam et al. |
| 2019/0046297 A1 | 2/2019 | Kopelman et al. |
| 2019/0099129 A1 | 4/2019 | Kopelman et al. |
| 2019/0125494 A1 | 5/2019 | Li et al. |
| 2019/0125497 A1 | 5/2019 | Derakhshan et al. |
| 2019/0152152 A1 | 5/2019 | O'Leary et al. |
| 2019/0175304 A1 | 6/2019 | Morton et al. |
| 2019/0262101 A1 | 8/2019 | Shanjani et al. |
| 2019/0298494 A1 | 10/2019 | Webber et al. |
| 2019/0314119 A1 | 10/2019 | Kopelman et al. |
| 2019/0343606 A1 | 11/2019 | Wu et al. |
| 2019/0388189 A1 | 12/2019 | Shivapuja et al. |
| 2020/0000553 A1 | 1/2020 | Makarenkova et al. |
| 2020/0100864 A1 | 4/2020 | Wang et al. |
| 2020/0100865 A1 | 4/2020 | Wang et al. |
| 2020/0100866 A1 | 4/2020 | Medvinskaya et al. |
| 2020/0155276 A1 | 5/2020 | Cam et al. |
| 2020/0188062 A1 | 6/2020 | Kopelman et al. |
| 2020/0214598 A1 | 7/2020 | Li et al. |
| 2020/0214801 A1 | 7/2020 | Wang et al. |
| 2020/0390523 A1 | 12/2020 | Sato et al. |
| 2021/0078357 A1 | 3/2021 | Venkatasanthanam et al. |
| 2021/0147672 A1 | 5/2021 | Cole et al. |
| 2023/0018058 A1* | 1/2023 | Mason ............ G16H 30/20 |

OTHER PUBLICATIONS

Liu, Q., et al., "Rapid prototyping in dentistry: technology and application," The International Journal of Advanced Manufacturing Technology, 2006, vol. 29 (3), pp. 317-335.

Matulka, R., "How 3D Printers Work," Department of Energy, Jun. 19, 2014, 16 pages, https://www.energy.gov/articles/how-3d-printers-work.

Wang, J., et al., "Modeling and Rendering of Heterogeneous Translucent Materials Using the Diffusion Equation," ACM Transactions on Graphics (TOG), 2008, vol. 27(1), pp. 1-18.

Yuan, J., et al., "Accurate and Computational: A review of color reproduction in Full-color 3d printing," Materials & Design, 2021, vol. 209, 17 pages.

Zardawi, F.M.M., "Characterisation of Implant Supported Soft Tissue Prostheses Produced With 3d Colour Printing Technology," (Doctoral dissertation, University of Sheffield), 2012, 274 pages.

Brett P. Conner, et al., "Making sense of 3-D printing: Creating a map of additive manufacturing products and services," Additive Manufacturing, 2014, vol. 1, pp. 64-76.

* cited by examiner

APPLIANCES FOR INTRAORAL DELIVERY OF AGENTS

CROSS REFERENCE

This application is a continuation of U.S. patent application Ser. No. 15/202,139 filed Jul. 5, 2016 which claims the benefit of U.S. Provisional Patent Application No. 62/189,303, filed on Jul. 7, 2015 and entitled "SYSTEMS, APPARATUSES AND METHODS FOR DRUG DELIVERY FROM DENTAL APPLIANCES WITH INTEGRALLY FORMED RESERVOIRS" and U.S. Provisional Patent Application No. 62/189,318, filed on Jul. 7, 2015 and entitled "DENTAL APPLIANCE HAVING ORNAMENTAL DESIGN."

The subject matter of the following patent applications is related to the present application: U.S. Application Ser. No. 62/189,259, filed on Jul. 7, 2015, entitled "MULTI-MATERIAL ALIGNERS"; U.S. Application Ser. No. 62/189,263, filed on Jul. 7, 2015, entitled "DIRECT FABRICATION OF ALIGNERS WITH INTERPROXIMAL FORCE COUPLING"; U.S. Application Serial. No. 62/189,291, filed on Jul. 7, 2015, entitled "DIRECT FABRICATION OF ORTHODONTIC APPLIANCES WITH VARIABLE PROPERTIES"; U.S. Application Ser. No. 62/189,271, filed on Jul. 7, 2015, entitled "DIRECT FABRICATION OF ALIGNERS FOR ARCH EXPANSION"; U.S. Application Ser. No. 62/189,282, filed on Jul. 7, 2015, entitled "DIRECT FABRICATION OF ATTACHMENT TEMPLATES WITH ADHESIVE"; U.S. Application Ser. No. 62/189,301, filed on Jul. 7, 2015, entitled "DIRECT FABRICATION CROSS-LINKING FOR PALATE EXPANSION AND OTHER APPLICATIONS"; U.S. Application Serial. No. 62/189,312, filed on Jul. 7, 2015, entitled "SYSTEMS, APPARATUSES AND METHODS FOR DENTAL APPLIANCES WITH INTEGRALLY FORMED FEATURES"; U.S. Application Ser. No. 62/189,317, filed on Jul. 7, 2015, entitled "DIRECT FABRICATION OF POWER ARMS"; and U.S. Application Ser. No. 62/189,380, filed on Jul. 7, 2015, entitled "DENTAL MATERIALS USING THERMOSET POLYMERS", the entire disclosures of which are hereby incorporated herein by reference.

BACKGROUND OF THE INVENTION

The present invention relates generally to dental appliances. More particularly, the invention relates to dental appliances for drug delivery with integrally formed reservoirs and dental appliances capable of displaying an ornamental design.

Dental appliances, such as braces (wire brackets) and retainers, have been used by teenagers and adults for several decades to straighten and maintain tooth positioning. However, these dental appliances, particularly wires and brackets, can be unsightly, uncomfortable, and cumbersome for the patient.

To address these issues with wires and brackets, removable polymeric shell appliances (e.g., aligners) were developed to straighten teeth. Clear aligners, such as the Invisalign® aligners manufactured by Align Technology, Inc. of San Jose, CA, are virtually invisible as well as comfortable. Such appliances may have a thin shell of plastic material that generally conforms to a patient's teeth but is slightly out of alignment with an initial or immediately prior tooth configuration. Placement of the appliance over the teeth applies controlled forces in specific locations to gradually move the teeth into the new configuration. Repetition of this process with successive appliances comprising new configurations eventually moves the teeth through a series of intermediate configurations or alignment patterns to a final desired configuration. A number of dental and periodontal therapies which may be desired or required by the patient may not be effectively utilized while the appliance is in place, in some instances. Such therapies may be prescribed by a practitioner to improve oral health or they may be requested by the patient for cosmetic purposes.

Unlike patients with braces, the patient wearing aligners has the freedom to eat anything he or she desires because the aligners are removable. Furthermore, removable aligners allow for easier care and cleaning of teeth. Patients are able to customize their braces by choosing the colors for the wires and brackets as well as the rubber bands that are worn with the wires and brackets. This ability to customize is especially attractive to teenagers. Thus, it would be desirable to provide aligners that are capable of being integrated with color and/or customized by the patient and/or also capable of providing therapies for a patient.

Furthermore, sometimes therapies and agents are provided with a variety of accessories and devices that are applied when the receiving appliance is removed from the patient's mouth. Thus, it would be desirable to provide an appliance that can provide a drug delivery method without removal of the appliance, which can eliminate the need for such removal and additional devices by integrating such therapies with the appliance.

SUMMARY OF THE INVENTION

According to an embodiment, an appliance is provided for intra-oral delivery of one or more agents to a patient. The appliance includes a shell forming a plurality of cavities shaped to receive teeth of a mouth of the patient, and a reservoir. The reservoir is integrally formed within the shell, and the reservoir is configured to receive, store and release an agent to the patient.

According to another embodiment, a method is provided for fabricating an appliance for intra-oral delivery of one or more agents to a patient. A digital model of the appliance is generated. The digital model includes a digital representation of a shell including a plurality of teeth receiving cavities and a digital representation of a reservoir integrally formed within the shell. Instructions are generated for fabricating the appliance with the shell and integrally formed reservoir using a direct fabrication technique, based on the digital model.

BRIEF DESCRIPTION OF THE DRAWINGS

The invention, together with further objects and advantages thereof, may best be understood by reference to the following description taken in conjunction with the accompanying drawings in which.

DETAILED DESCRIPTION OF THE PREFERRED EMBODIMENTS

Figure 1:
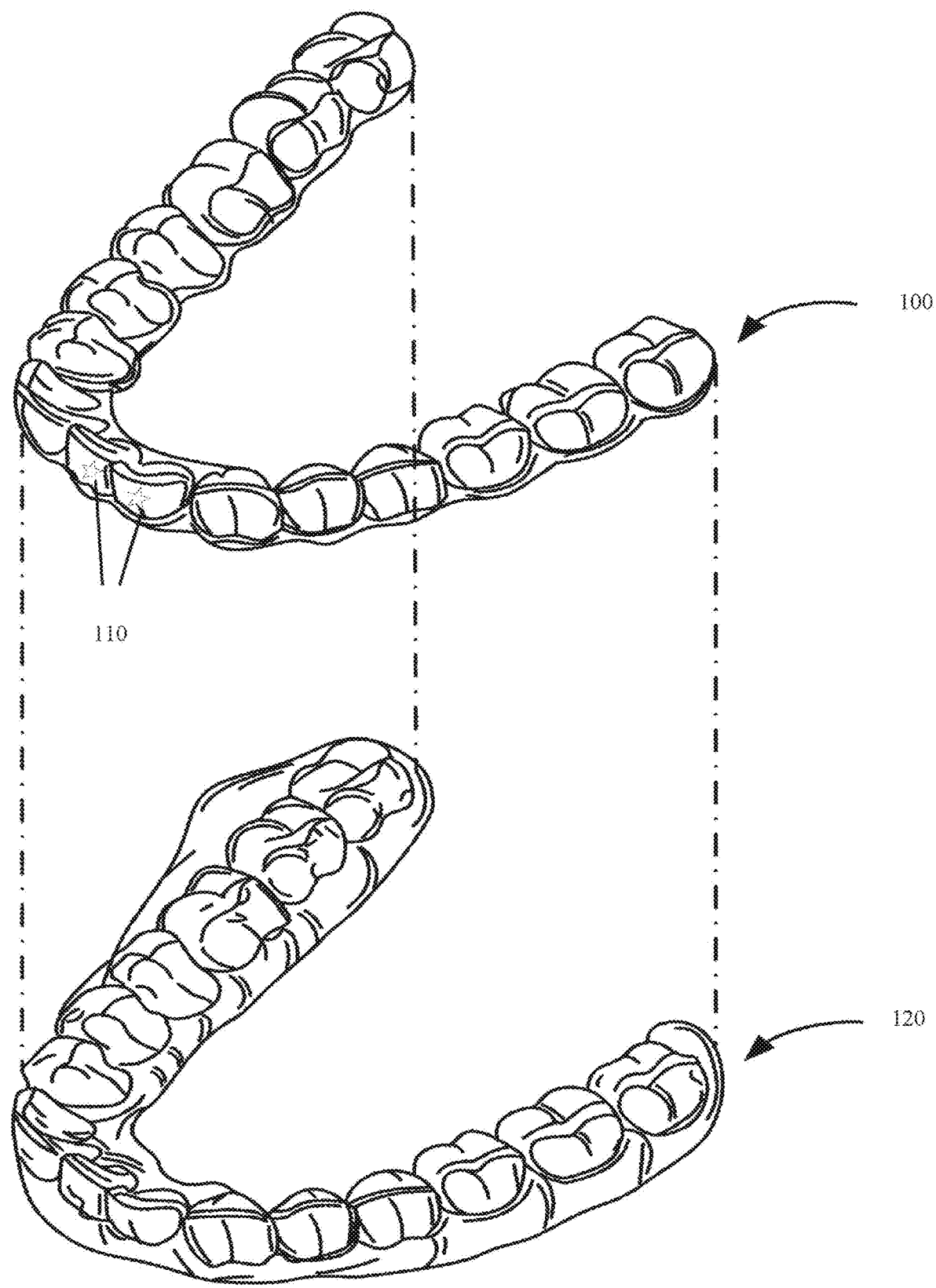
FIG. 1 is a perspective view of a dental appliance in accordance with an embodiment.

The present invention relates generally to dental appliances. More particularly, the appliance relates to dental appliances capable of displaying customizable ornamental designs and/or labels and for drug delivery. Dental appliances, including retainers, positioners, and aligners, with integrally formed reservoirs are capable of drug delivery as well as displaying integrated designs and colors. Integrated designs and colors, particularly those that are selected or even created by the patient, provide the patient with the ability to customize the appliance. These dental appliances provide patients with even more opportunity for customization than colored wired and brackets.

A reservoir can be any structure or material containing an agent for treating a patient, such as a layer, coating, recess, cavity, chamber, membrane, scaffold, and the like. As used herein, "integrally formed reservoir" may refer to a reservoir formed as a single unitary or monolithic piece with another appliance component (e.g., an appliance shell with teeth receiving cavities), such that the reservoir cannot be separated from the appliance without damaging or destroying the appliance component. An integrally formed reservoir may be differentiated from a reservoir that is formed and/or provided separately from the appliance and is subsequently coupled to the appliance component (e.g., by adhesives, fasteners, coating, layering, spraying, painting, dipping, etc.). In some embodiments, an integrally formed reservoir is concurrently formed with another appliance component in a single manufacturing or fabrication step, such that the same fabrication machine and/or fabrication process is used to produce both the reservoir and the appliance component. Accordingly, an integrally formed reservoir may be differentiated from a reservoir that is formed prior to or after the appliance component is formed and may be differentiated from a reservoir that is formed using a different fabrication process than the process used to form the appliance component. For example, the various direct fabrication methods discussed herein can be used to produce both the appliance component and the integrally formed reservoir concurrently in a single fabrication step.

An aligner is a relatively thin shell of material that generally conforms to a patient's teeth but is slightly out of alignment with the current tooth configuration. The material of the aligner is typically a polymeric material that has resilient properties. Dental treatments using aligners typically involve repositioning misaligned teeth and changing bite configurations for improved cosmetic appearance and dental function. Such repositioning with aligners can be accomplished by applying controlled forces to one or more teeth over a period of time.

As noted above, placement of such an appliance over the teeth provides controlled forces in specific locations to gradually move the teeth into a new configuration. Repetition of this process with successive appliances that provide progressive configurations eventually move the teeth through a series of intermediate arrangements to a target, prescribed, or desired arrangement. An example of such a system is described in U.S. Pat. No. 5,975,893, which is hereby incorporated herein by reference.

Once the teeth have been repositioned to a final desired arrangement, they typically need to be maintained in the desired arrangement to prevent the teeth from moving out of the desired arrangements. Such maintenance can be accomplished by wearing a retainer, which similar to an aligner can also be a polymeric shell appliance. The retainer may, but does not have to, impart force to any of the teeth (e.g., for re-positioning). In some embodiments, the appliance serves the purpose of receiving teeth to enable methods of drug delivery to the patient rather than repositioning the patient's tooth or teeth in addition to methods of drug delivery. The appliances described herein may be fabricated with integrally formed reservoirs to achieve methods of drug delivery alone or in combination with repositioning the patient's tooth or teeth. In some aspects, the reservoir can be positioned away from portions of the appliance used to apply forces to the teeth.

Embodiments of a dental appliance having an ornamental design thereon will be described herein. In an illustrated embodiment, the dental appliance 100 has a geometry for receiving teeth. As shown in FIG. 1, the dental appliance 100 can be configured to fit over an entire dental arch 120. In other embodiments, the dental appliance may be designed to fit over some or all of the teeth in the upper or lower jaw. The dental appliance 100 can be fabricated from a polymeric shell, or formed from another material, and include a number of cavities shaped to receive corresponding teeth.

In some embodiments described herein, systems, methods and devices for drug delivery tooth receiving appliances with integrally formed reservoirs include an appliance for intra-oral delivery of one or more agents to a patient. Such appliances can include a shell forming a plurality of cavities shaped to receive teeth of a mouth of the patient, and a reservoir that is integrally formed within the shell. The reservoir is configured to receive, store and release an agent to the patient. The shell may encompass the reservoir such that the volume of the reservoir is less than the volume of the shell in the absence of the reservoir. In some aspects of the embodiments, the shell further includes a channel integrally formed within the shell. In some aspects of the embodiments, the shell and the reservoir comprise a first material, or the shell comprises the first material and the reservoir comprises a second material, or the reservoir comprises the first material and the second material. In some aspects of the embodiments, the reservoir is hollow or filled with a porous material, the porous material comprising the second material or a third material. In some aspects of the embodiments, the second or the third material is a degradable material or a material configured to release an agent by diffusion. In some aspects of the embodiments, the porous material further comprises pores having a diameter of about 50 μm, about 30 μm, about 20 μm, about 15 μm, about 10 μm, about 5 μm, about 1 μm, about 500 nm, about 100 nm, about 10 nm, or about 1 nm. In some aspects of the embodiments, the porous material further comprises pores having the same diameter or having different diameters.

The porous properties of a material can be used as a method of controlling diffusion of an agent from the integrally formed reservoir. For example, larger pores, such as 50 μm may be selected as the diameter of the pores in the porous material when the agent is of a small molecular weight, thus the porous material is configured for a higher rate of diffusion of the agent through the pores and into the intraoral cavity. As another example, medium-sized pores, such as 25 μm may be selected as the diameter of the pores in the porous material when the agent is of a small molecular weight, thus the porous material is configured for a medium rate of diffusion of the agent through the pores and into the intraoral cavity. The plurality of agents described herein or others known to one of skill in the art can comprise a plurality of molecular weights. The pore sizes described herein or others known to one of ordinary skill in the art of the porous material can be selected during the methods of manufacturing and/or fabricating the shell in order to facilitate a desired rate of delivery and/or desired rate of diffusion of the agent from the integrally formed reservoir. The first material may be selected from a material as described herein or known to one of ordinary skill in the art and often, but is not limited to, lacking degradable properties.

In some aspects of the embodiments, the reservoir comprises at least one port, wherein the at least one port is an outlet port, an inlet port or a universal port. In some aspects of the embodiments, the outlet port and the universal port are configured to release an agent into the mouth of the patient in response to a stimulus or to release an agent into the channel of the shell in response to a stimulus. In some aspects of the embodiments, the agent is a pharmaceutical composition, a chemical, a gene, a polypeptide, an enzyme, a biomarker, a dye, a compliance indicator, an antibiotic, an analgesic, a medical grade drug, a chemical agent, a bioactive agent, an antibacterial, an antibiotic, an anti-inflammatory agent, an immune-suppressive agent, an immune-stimulatory agent, a dentinal desensitizer, an odor masking agent, an immune reagent, an anesthetic, a nutritional agent, an antioxidant, a lipopolysaccharide complexing agent or a peroxide. In some embodiments where the appliance is generated by a fabrication machine according to a set of fabrication instructions, the fabrication instructions comprise the steps of generating a digital model of the shell, the digital model including the reservoir integrally formed into the shell, and fabricating the shell having the reservoir integrally formed into the shell during a single fabrication step.

In some embodiments, the dental appliance 100 is an orthodontic appliance, such as an aligner, configured to move teeth from one position to a successive position. In other embodiments, the dental appliance 100 is an appliance, such as a retainer, configured to maintain the positioning of the teeth.

According to embodiments, the dental appliance includes a removable orthodontic tooth positioning appliance having teeth receiving cavities shaped to directly receive at least some of the patient's teeth and apply a resilient positioning force to the patient's teeth. An appliance can fit over some or all teeth present in an upper or lower jaw. In some cases, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment.

Teeth that are moved can also serve as a base or anchor for holding the appliance as it is worn by the patient. Typically, no wires or other means will be provided for holding an appliance in place over the teeth. In some cases, however, it may be desirable or necessary to provide individual anchors on teeth with corresponding receptacles or apertures in the appliance so that the appliance can apply a selected force on the tooth. Exemplary appliances are described in numerous patents and patent applications assigned to Align Technology, Inc. including, for example, in U.S. Pat. Nos. 6,450,807, and 5,975,893, as well as on the company's website, which is accessible on the World Wide Web (see, e.g., www.invisalign.com). The aforementioned patents are hereby incorporated herein for all purposes.

An appliance can be designed and/or provided as part of a set of a plurality of appliances. In such an embodiment, each appliance may be configured such that a tooth-receiving cavity has a geometry corresponding to an intended intermediate or final tooth arrangement. The patient's teeth can be progressively repositioned from an initial tooth arrangement to a target tooth arrangement by placing a series of incremental position adjustment appliances over the patient's teeth. A target tooth arrangement is a planned tooth arrangement (e.g., a planned temporary or final arrangement) selected for the patient's teeth at a specific stage of the planned orthodontic treatment. A target arrangement can be one of many intermediate arrangements for the patient's teeth during the course of orthodontic treatment, which may include where surgery is recommended, where inter-proximal reduction (IPR) is appropriate, where a progress check is scheduled, where anchor placement is best, where palatal expansion is desirable, etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

The adjustment appliances can be generated all at the same stage or in sets or batches, e.g., at the beginning of a stage of the treatment, and the patient wears each appliance until the pressure of each appliance on the teeth can no longer be felt or has resulted in the maximum amount of expressed tooth movement for that given stage. A plurality of different appliances (e.g., set) can be designed and even fabricated prior to the patient wearing any appliance of the plurality. After wearing an appliance for an appropriate period of time, the patient replaces the current appliance with the next appliance in the series until no more appliances remain. The appliances are generally not affixed to the teeth and the patient may place and replace the appliances at any time during the procedure (e.g., patient-removable appliances).

The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

According to an embodiment, as shown in FIG. 1, the ornamental design 110, which can include one or more designs as well as labels, can be integrated with the appliance 100. Some patients may choose to integrate the design 110 particularly in the anterior or social six portion of the appliance 100 so that the design 110 can be readily seen by others when the appliance 100 is worn by a patient. The term "social six" refers to the six teeth at the front of the upper arch that are seen the most when a person is talking or smiling. It will be understood that in FIGS. 1-4, a star shape is provided as the ornamental design, but that any image (including words) can be used as the ornamental design, as the ornamental can be customized by a patient in some embodiments.

In other embodiments, the ornamental design or label 110 can be positioned on different parts of the appliance 100. The design 110 can be either colored or gray scale and can be selected or even customized by the patient. The color(s) can also be customized. It will be understood that the design 110 shown in FIG. 1 is an exemplary design and that, in other embodiments, the design 110 can be different and also positioned on a different area of an appliance 100.

As will be explained in more detail below, the design 110 can be integrated with the appliance 100 in a variety of different ways. For example, the design 110 can be printed onto the appliance 100 or heat energy can be directed at the appliance 100 to form the design 110 on the appliance 100. In other embodiments, the ornamental design can be mechanically attached to the appliance or mechanically etched onto a surface of the appliance.

In an embodiment where the dental appliances 100 are orthodontic appliances, such as aligners, in a series of appliances, the design 110 can be customized by the patient for each individual appliance in the series. Furthermore, in an embodiment where the design 110 is mechanically attached to the appliance, the patient can have a set of different designs that can be interchangeably attached to the appliance(s), as will be explained in more detail below.

The appliance 100 can be fabricated using a variety of different suitable methods, including thermoforming, casting, 3D printing, stereolithography, milling, direct fabrication etc. For example, as will be described in more detail below, methods for making the appliances can include thermoforming a polymer sheet into an aligner by heating the sheet and then molding the sheet to a particular con-figuration. Exemplary methods for fabricating the appliances are described in numerous patents and patent applications assigned to Align Technology, Inc. including, for example, in U.S. application Ser. No. 13/186,374 as well as on the company's website, which is accessible on the World Wide Web (see, e.g., www.invisalign.com). The aforementioned patent application is hereby incorporated herein for all purposes.

Figure 2A:
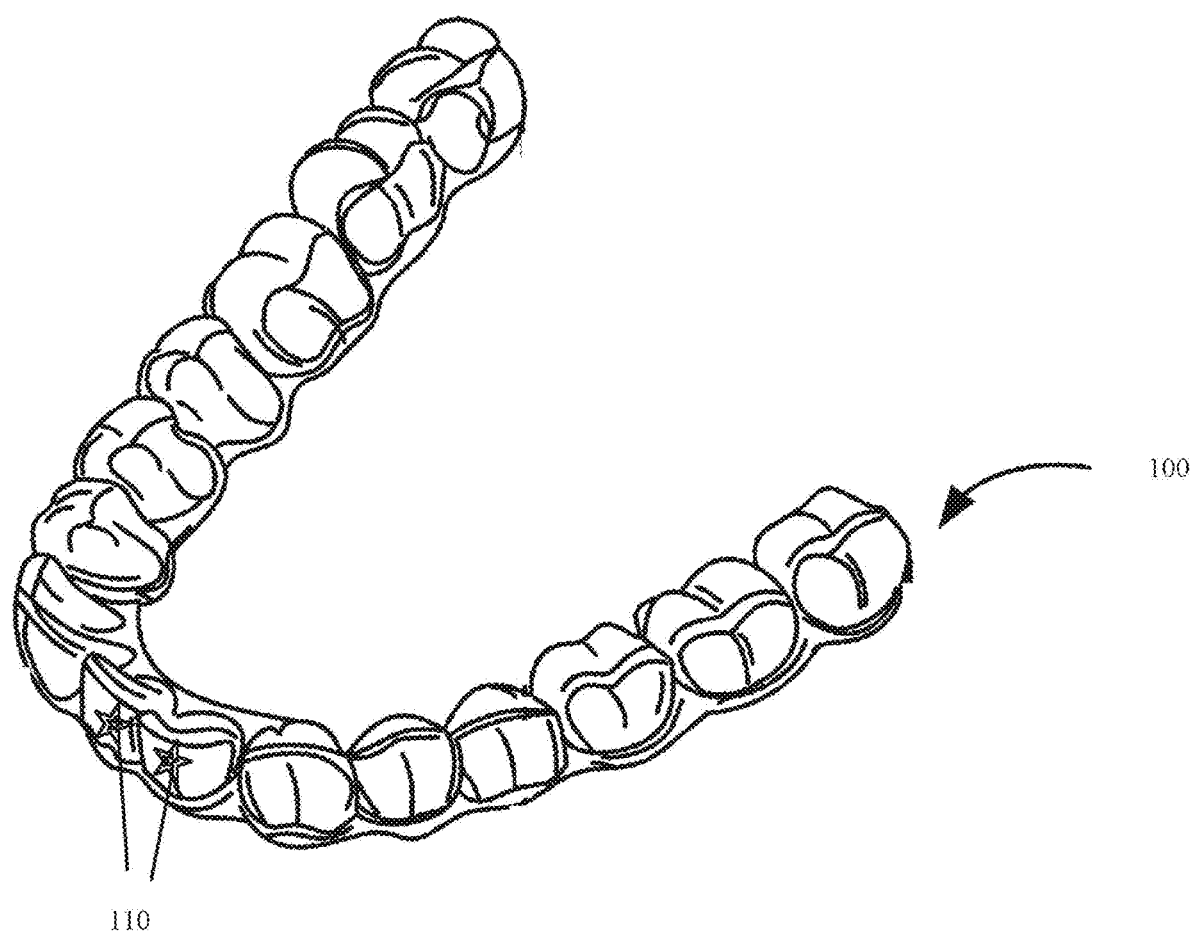
FIG. 2A is a perspective view of a dental appliance in accordance with another embodiment.
Figure 2B:
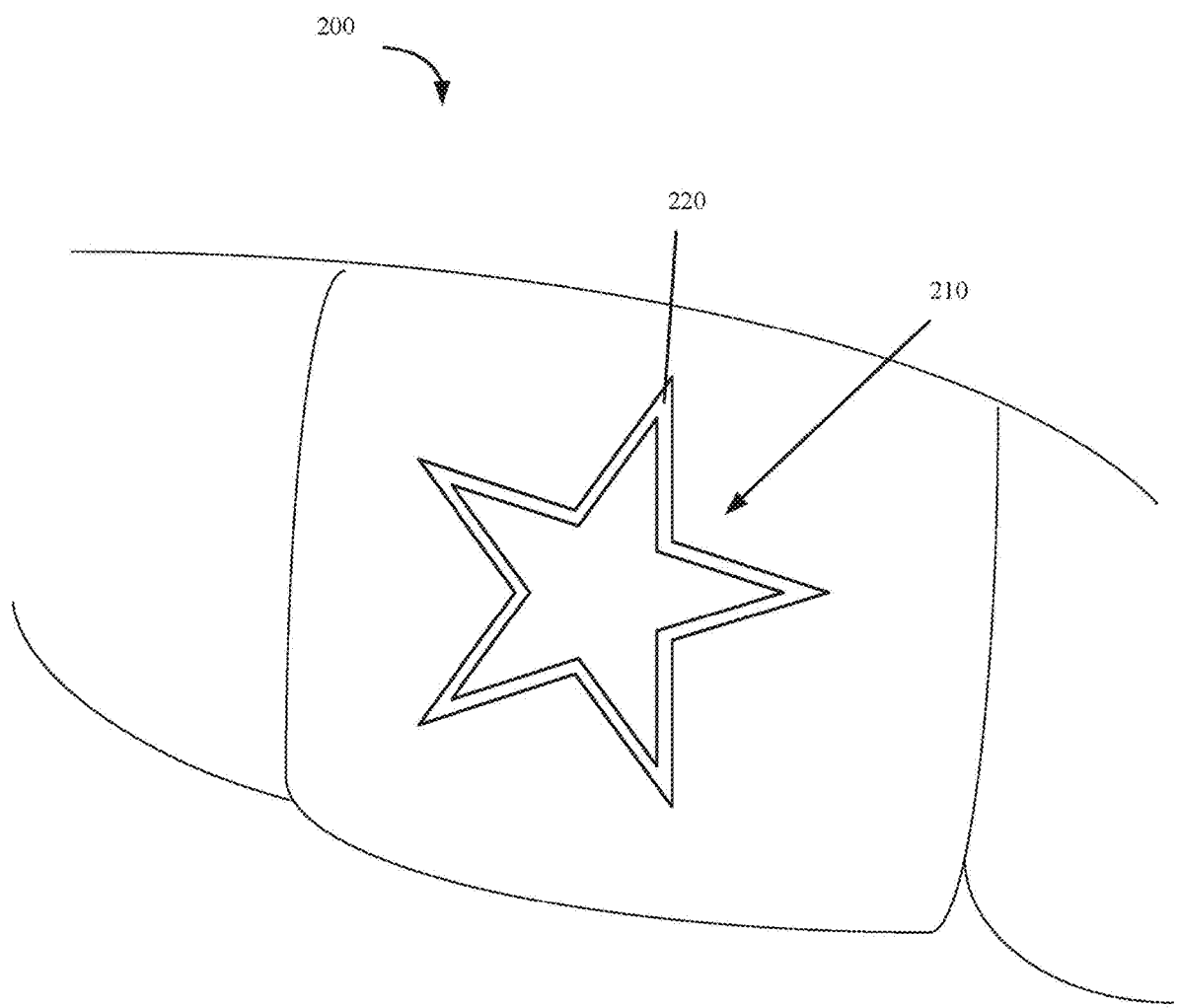
FIG. 2B is a detailed view of an ornamental design on the dental appliance shown in FIG. 2A.

FIGS. 2A and 2B show a dental appliance 200 formed from a polymeric material having an ornamental design 210 that is formed by removing portions of the polymeric material to form one or more grooves or recesses, which can be filled with colored ink. The grooves or recesses can be formed by methods, such as by etching or laser scribing. The appliance 200 can display an ornamental design 210 that can be selected or customized. According to an embodiment, the ornamental design 210 can be laser scribed onto a surface of the appliance 200 by directing laser energy to the appliance 200. Alternatively, the design 210 can be etched or milled onto a surface of the appliance 210. In still other embodiments, the appliance 200 can be fabricated on a mold with positive features to result in grooves formed in the appliance 200. It will be understood that the ink needs to have sufficient flexibility to flex with the appliance 200. If the ink does not have sufficient flexibility, the design 210 crack and/or shear off from the appliance 200.

The design 210 can also be colored by first etching or sintering the design 210 to form a groove, series of grooves, or recess(es) 220 to form the design 210. The groove(s) or recess(es) can then be filled with colored ink. The ink can include one or more colors, as desired. Thus, the design 210 can be gray scale if no ink is used or can be monochromatic or multi-colored, depending on the desired design. As noted above, the design 210, including the color(s), is entirely customizable. Biocompatible ink made of biocaompatible curable liquids can be used to provide the design 210 with color. For example, grooves or recesses can be filled with biocompatible ink. In one embodiment, one color can be used to fill each groove. It will be understood that the same color can also be used to fill more than one groove, depending on the particular design. It will be understood that, in some embodiment, the appliance 200 can be formed from a multilayer sheet of polymeric material such as the one described below with reference to FIGS. 3A and 3B.

In some embodiments, a polymeric shell appliance can be provided with an ornamental design 110, 210 to indicate compliance with the treatment plan. Appliance compliance indicators are described in U.S. Pat. No. 7,854,609, which is hereby incorporated by reference herein in its entirety for all purposes. Since polymeric shell appliances are removable by the patient, the dentist or orthodontist must rely on the patient to wear the appliance and comply with the prescribed treatment plan. According to an embodiment, the ornamental design 110, 210 can change based on the controlled-release of a colored material that is encapsulated within a membrane or reservoir attached to the appliance 100, 200. The membrane or reservoir can cover all or a portion of the design 110, 210 that is filled with a colored controlled-release material and the membrane or reservoir has at least one small pore in it. When the appliance is worn by the patient, the small pore(s) in the membrane will gradually open and allow the colored controlled-release material within the membrane to dissipate. In some embodiments, the membrane is formed of a material that will warm up (in the patient's mouth) and the colored substance will also warm up so that it can flow out of the premade pore in the membrane.

In other embodiments, the membrane is formed of a material that will stretch with time as the appliance is worn by the patient, allowing the colored substance to flow out. If the membrane encapsulating the colored controlled-release material is in a region that will stretch when inserted, the stretch of the membrane could open a slit in the membrane to allow the color to disappear while the slit is stretched due to the flexing of the appliance and the membrane due to the forces being applied by the appliance to move the teeth. Once the teeth have been moved to the prescribed position for the particular appliance, the membrane will no longer stretch and the color will be gone.

Thus, the patient will know that the appliance has been worn long enough when some aspect of the design 110, 210 has faded away. In one exemplary embodiment, the design 110, 210 can include a permanent portion of the design spelling "happy" and another portion of the design covered by a membrane with pores spelling "be" before the "happy" portion. The pores can expand under body temperature and allow the colored controlled-release material in the "be" portion to dissipate. Thus, when the patient has worn the appliance for the appropriate amount of time, the "be" will disappear and the design 110, 210 will only read "happy". In other embodiments, the design 110, 210 can change in different ways. For example, the design 110, 210 could disappear completely, change color, or could turn into a different design. According to other embodiments, the interaction of heat and/or saliva with a substance causes a colored design 110, 210 to appear when the appliance has been worn long enough to indicate compliance.

In some embodiments, the compliance indicator has a clear, tooth-colored, or esthetically pleasing polymer reservoir well, chamber, or housing. A transparent or translucent semi-permeable membrane separates the content within the reservoir chamber from the external oral environment which may comprise degradable materials and/or porous materials as described herein. The content(s) of the agent within the integrally formed reservoir depends on the overall strategy to monitor compliance. For example, contents diffuse out from the integrally formed reservoir, through the membrane, into the external environment. The content can be an FDA approved visible dye which diffuses from the chamber, through the membrane, and into the external oral environment. When the content is emptied, the content color diminishes in brightness and value. Colorants that are permitted for direct addition to human food by the US FDA include annatto extract, beta-carotene, beet powder, canthaxanthin, caramel color, carrot oil, cochineal extract (carmine); cottonseed flour, fruit juice, paprika, riboflavin, saffron, turmeric, vegetable juice, FD & C Blue No. 1 (brilliant blue) and No. 2 (indigotine FD & C Green No. 3 (fast green FCF), FD & C Red No. 3 (erythrosine) and No. 40 (allura red), FD & C Yellow No. 5 (tartrazine) and No. 6 (sunset yellow). Other food colorants such as those found at FDA's Center for Food Safety and Applied Nutrition website: http://www.cfsan.fda.gov/.abaut.dmsicol-toc.html can be used as well.

In another aspect, matter from the external environment diffuse in, and reacts with the contents within the integrally formed reservoir. For example, glucose molecules from the external environment can diffuse through the membrane, and react with enzymes inside the content and the resultant enzymatic products interact with other reactants inside the content to cause color change. As more glucose molecules diffuse in, content color increases in brightness and value. A convenient enzyme system is glucose oxidase and horseradish peroxidase. The first enzyme, glucose oxidase, catalyzes the oxidation of glucose to form gluconic acid and hydrogen peroxide. Hydrogen peroxide then reacts with 3-3,5,5'-tetramethylbenzidine (TMB) under catalytic action of horseradish peroxidase to convert yellow 1 MB to green. Other colorants, such as potassium iodide (green to brown) may also be used. These enzymes can be immobilized within the integrally formed reservoir. The rate of reaction, and hence color change, can be controlled by selecting the permeability of the membrane, the concentration of reactants inside the integrally formed reservoir, and the method of delivery. The rate of reaction or concentration of the glucose molecules can also be detected through spectroscopy or other analytical testing. Test results will correlate with compliance to treatment.

A compliance indicator can be a dye encapsulated in a polymer or other compound as described herein or the compliance indicator can be released in the presence of oral fluids. The dye can be colorants that react with the oral fluids and that are released from the polymer. The polymer can be porous polymer such as monolithic porous polymer (currently used in chromatography), PVS, a high internal phase emulsion (RIPE polymer currently used in drug release), or any, macroporous polymer. The dyed polymer will be constructed into a small button that can be bonded to the exterior of the aligner. The amount of dye loss will correspond with the amount of time the aligner was in use. The pore size of the polymer and the particle size of the dye will affect the rate of diffusion of dye from the button to the oral fluids environment and depending on compliance needs, these factors can be controlled.

According to other embodiments, as shown in FIGS. 3C-3H, a reservoir is integrally formed with a polymeric shell appliance for drug delivery. In some embodiments, the systems, methods and devices for drug delivery tooth receiving appliances with integrally formed reservoirs include a method for fabricating an appliance for intra-oral delivery of one or more agents to a patient, the method comprising: generating a digital model of the appliance, the digital model comprising a digital representation of a shell comprising a plurality of teeth receiving cavities and a digital representation of a reservoir integrally formed within the shell; and generating instructions for fabricating the appliance with the shell and integrally formed reservoir using a direct fabrication technique, based on the digital model. In some aspects, a direct fabrication technique comprises one or more of: stereolithography, selective laser sintering, fused deposition modeling, or 3D printing. In some aspects, the instructions are configured to control a fabrication machine to form the reservoir concurrently with the shell.

As noted in commonly owned U.S. Pat. No. 6,607,382 entitled "Methods and systems for concurrent tooth receiving and substance delivery," the content of which is incorporated herewith, the receiving of teeth may be accomplished with the use of a series of removable elastic positioning appliances such as the Invisalign® system available from Align Technology, Inc., the assignee of the present invention. Such appliances have a thin shell of elastic material that generally conforms to a patient's teeth but is slightly out of alignment with an initial or immediately prior tooth configuration. Placement of the elastic positioner over the teeth applies controlled forces in specific locations to gradually move the teeth into the new configuration. Repetition of this process with successive appliances comprising new configurations eventually moves the teeth through a series of intermediate configurations or alignment patterns to a final desired configuration. A full description of an exemplary elastic polymeric positioning appliance is described in U.S. Pat. No. 5,975,893, and in published PCT application WO 98/58596, and the content of these documents are incorporated by reference for all purposes. The appliance is effective in receiving teeth when it is placed over the patient's teeth. Removal of the appliance for any reason may interrupt the treatment plan and lengthen the overall period of treatment. Therefore, removal of the appliance should be minimized for effective and timely treatment in some embodiments. However, a number of dental and periodontal therapies which may be desired or required by the patient may not be effectively utilized while the appliance is in place. Such therapies may be prescribed by a practitioner to improve oral health or they may be requested by the patient for cosmetic purposes.

The '382 patent discloses devices, systems and methods for orthodontic treatment using elastic receiving appliances while concurrently providing dental and periodontal therapies. Such therapies are traditionally provided with the use of a variety of accessories and devices which are applied when the receiving appliance is removed from the patient's mouth. The '382 system eliminates the need for such removal and additional devices by incorporating these therapies into the receiving appliance. United States Patent Application 20040115587, the content of which is incorporated herewith by reference, discloses an orthodontic treatment involving applying force to receive teeth and administering a tissue remodeling and/or an angiogenic substance(s) to the periodontal tissue surrounding the teeth to be moved.

As noted in commonly owned U.S. Pat. No. 8,439,674 entitled "Systems and Methods for Intra-oral Drug Delivery," the content of which is incorporated herein by reference, the receiving of teeth may be accomplished with the use of a series of removable elastic positioning appliances such as the Invisalign® system available from Align Technology, Inc., the assignee of the present invention. The '674 patent discloses systems and methods for intraoral delivery of drugs from at least one of the previously disclosed removable elastic positioning appliances.

In some aspects of the embodiments, the tooth receiving appliance is formed with an integrated reservoir using any of the direct fabrication methods described herein. A reservoir is integrally formed into the appliance during a single manufacturing step whereby the reservoir is fabricated into the aligner shell. In this case, the reservoir is encompassed within the walls of the aligner shell, e.g., between an internal surface of a wall near the teeth and an external surface of a wall away from the teeth. Often the integrally formed reservoir comprises volume within the shell less than the volume of the shell in the absence of the reservoir. Accordingly, the volume of the integrally formed reservoir may be a portion of the volume of the shell in the absence of the reservoir, for example, expressed as a ratio of integrally formed reservoir volume to shell volume. The appliances described herein are not limited to a single integrally formed reservoir and any description of an integrally formed reservoir herein may be applicable to a plurality of integrally formed reservoirs within the shell (e.g., two, three, four, five, six, seven, eight, nine, ten, or more reservoirs within the single shell). The integrally formed reservoir may have any of the geometries described herein, and integrally formed reservoir geometries may be selected in accordance with the patient treatment plan. Such geometries may be determined during the methods described herein. Features and characteristics of the integrally formed reservoir are described further herein.

Figure 3A:
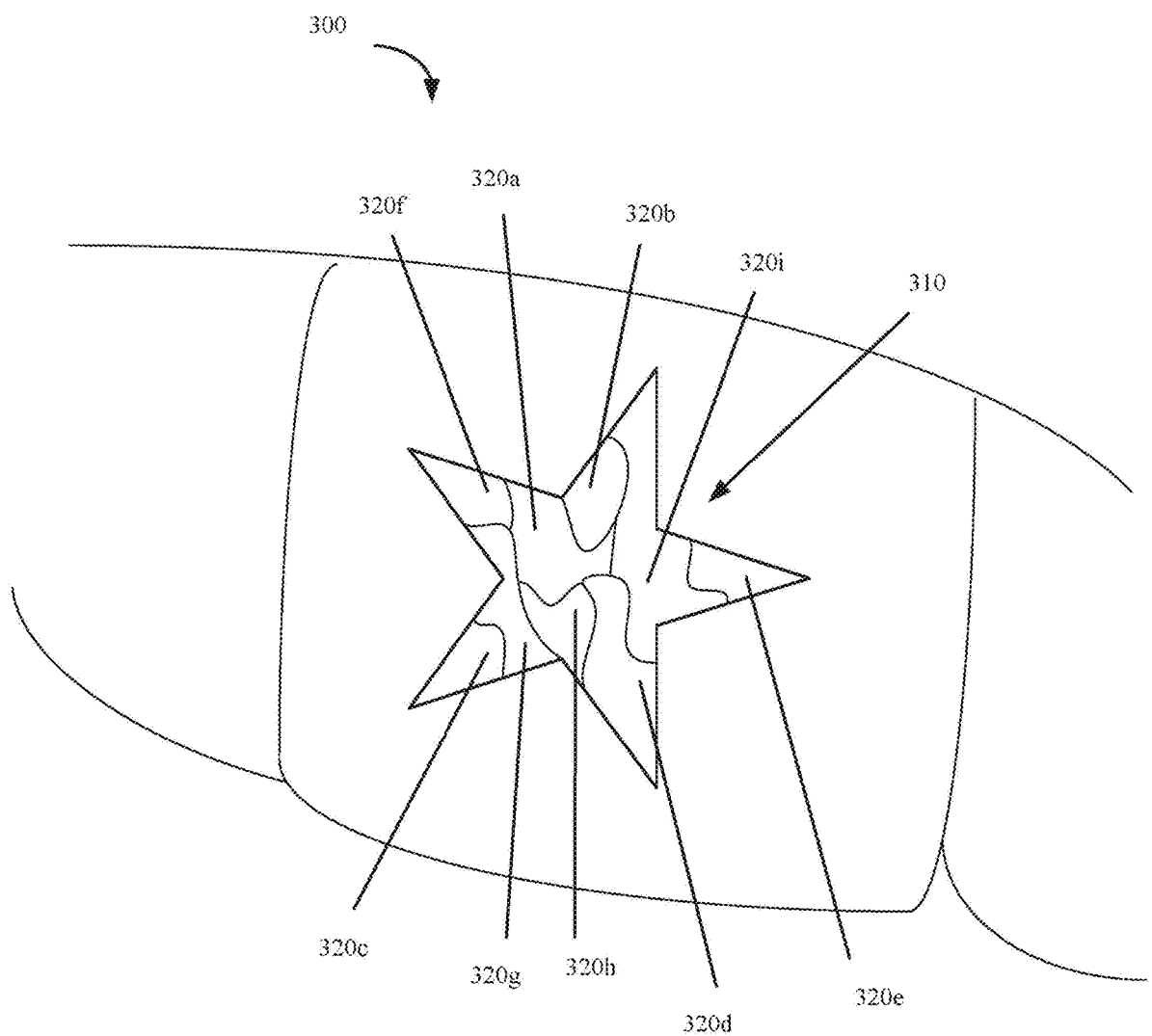
FIG. 3A is a front view of a dental appliance in accordance with yet another embodiment.
Figure 3B:
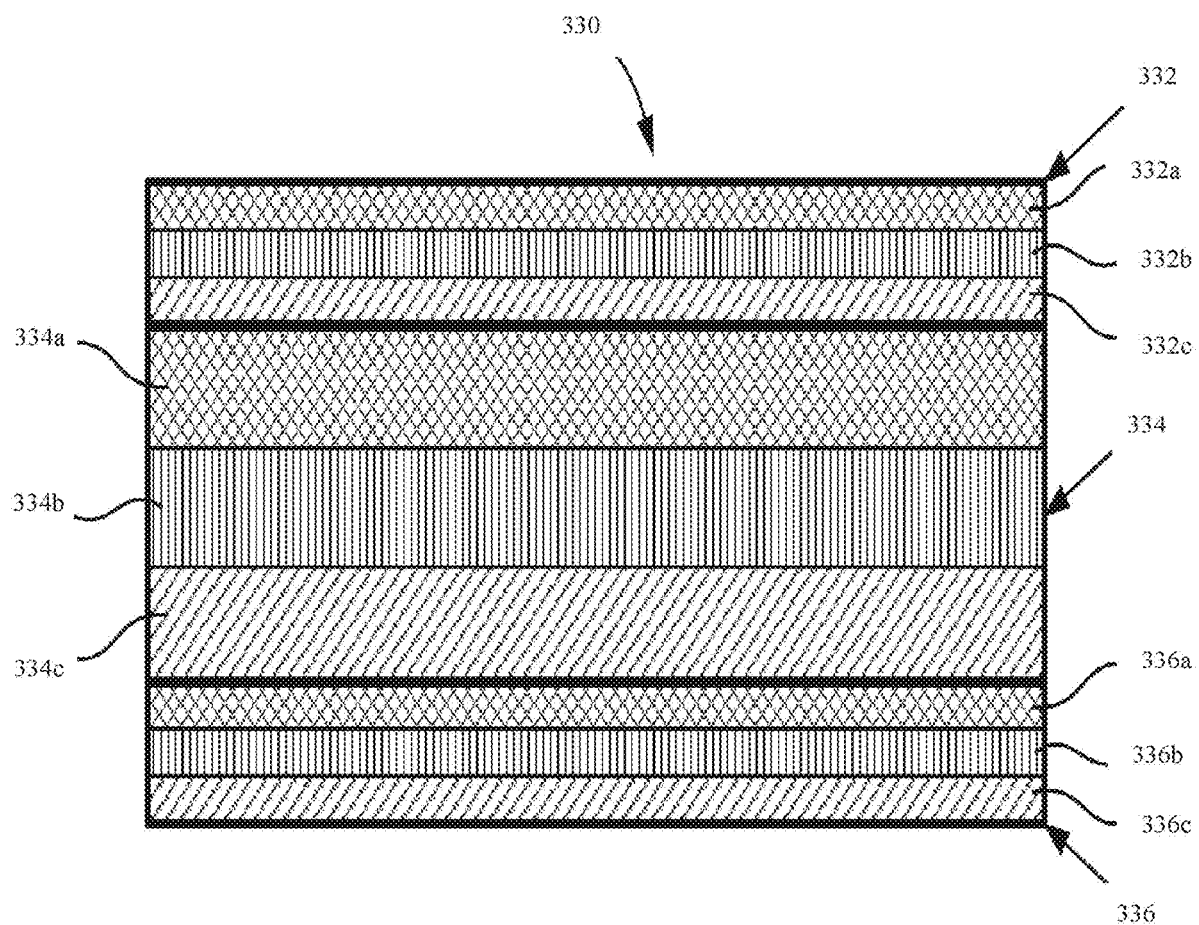
FIG. 3B is a side cross-sectional view of a multilayer polymer sheet used to form the dental appliance shown in FIG. 3A.
Figure 3C:
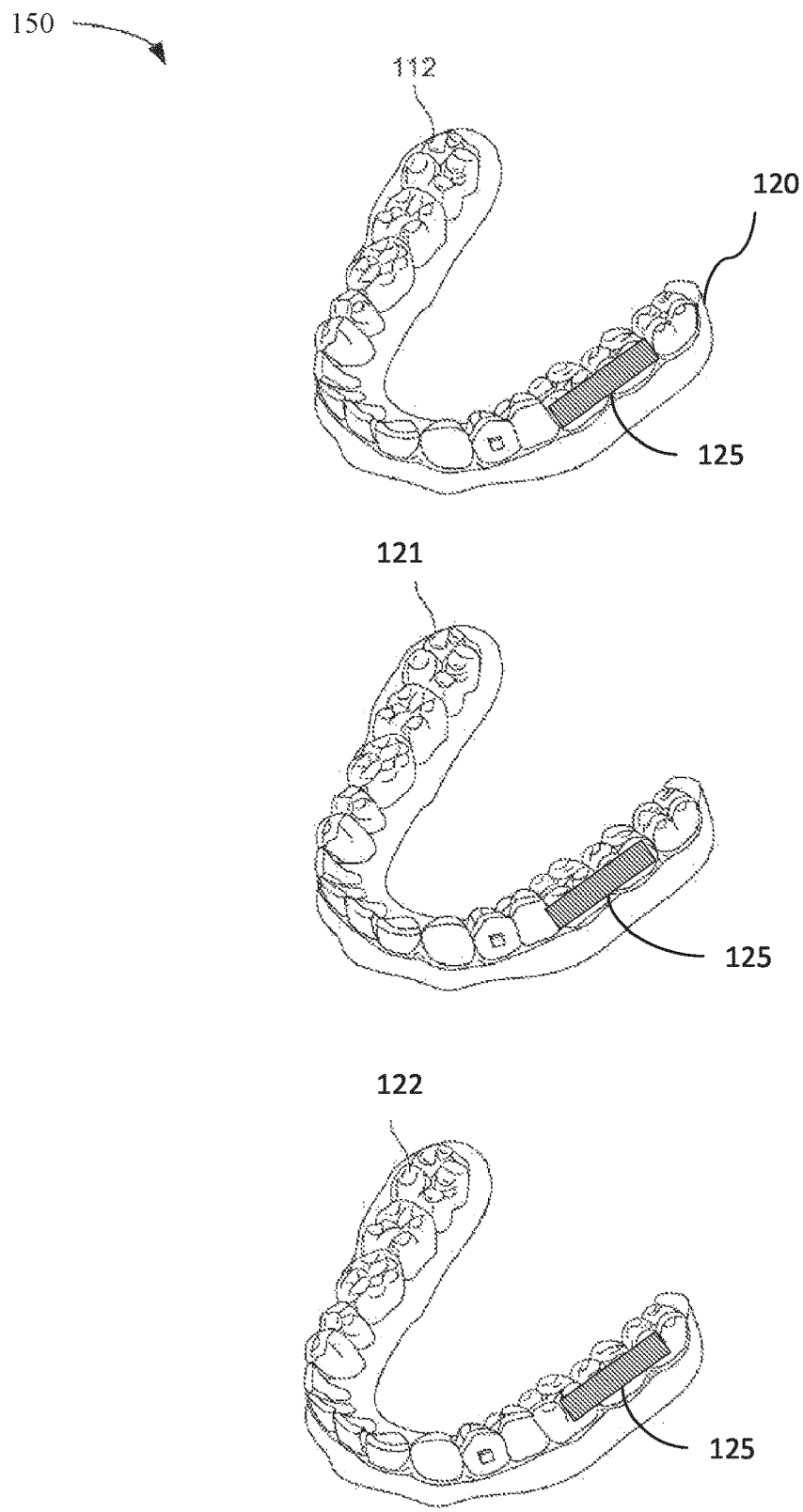
FIG. 3C illustrates a tooth receiving appliance comprising a shell with an integrally formed reservoir, in accordance with an embodiment.

FIG. 3C illustrates a tooth receiving appliance 112 comprising a shell 120 with an integrally formed reservoir 125. The tooth receiving appliance 112 is a portion of the tooth receiving system 150. Any of the appliances described herein can be designed and/or provided as part of a set of a plurality of appliances used in a tooth receiving system 150. The reservoir may be integrally formed in any position within the shell of the appliance such that release of an agent from the reservoir is performed in accordance with the patient's treatment plan. Placement of the reservoir within the shell may be designed as a part of the patient's treatment plan so as to not interfere with the intermediate or final tooth arrangement intended for the appliance. For example, the tooth receiving system 150 can include a first appliance 112 corresponding to an initial tooth arrangement with a reservoir integrally formed within the shell of the appliance at a first location, one or more intermediate appliances 121 corresponding to one or more intermediate arrangements and each of the one or more intermediate appliances with a reservoir integrally formed within the shell of the appliance at a location different or the same from the first location within the shell of the first appliance 112, and a final appliance 122 with a reservoir integrally formed within the shell of the appliance at a location different from the first location or the same as the first location and the one or more intermediate locations corresponding to a target arrangement. An exemplary, but not limiting, location of the integrally formed reservoir 125 is depicted in the final appliance 122. A target tooth arrangement can be any planned resulting arrangement for the patient's teeth that follows one or more incremental receiving stages. Likewise, an initial tooth arrangement can be any initial arrangement for the patient's teeth that is followed by one or more incremental receiving stages.

Any appliance for use at one or more of the incremental receiving stages of the tooth receiving system may include an integrally formed reservoir. Design of a tooth receiving system can include but is not limited to, planning a placement of the integrally formed reservoir within any of the appliances of the tooth receiving system used during one or more of the incremental receiving stages, planning the number of appliances to comprise an integrally formed reservoir for use during one or more of the incremental receiving stages, planning the order of use of appliances comprising an integrally formed reservoir and the like.

In some aspects of the embodiments, the integrally formed reservoir may have any of a plurality of geometries including shapes, dimensions, angles and the like. Shapes of the integrally formed reservoir include, but are not limited to, a circle, an oval, an ellipse, a curved structure with a complex shape, a triangle, a square, a rectangle, a polygon, a pentagon, a hexagon, a heptagon, and the like. The integrally formed reservoir may have walls which are straight or curved, as such, the walls of the integrally formed reservoir may or may not form angles. Geometries of the integrally formed reservoir may distribute through a single plane (e.g., x-axis, y-axis, z-axis) of the shell or may distribute through a plurality of planes through the aligner shell. In some aspects, the reservoir can be contained wholly within the interior of the shell such that no portion is directly exposed to the intraoral environment. In some other aspects, the reservoir can be partially contained within the interior such that one or more portions are directly exposed to the intraoral environment.

The dimensions of the integrally formed reservoir accord with the shape of the integrally formed reservoir, the integrally formed reservoir may have a volume such that the integrally formed reservoir may be filled through the inlet port with an agent comprising a drug and an aqueous solution as described herein. In some cases, the volume is devoid and empty such that the integrally formed reservoir may be filled through the inlet port with an agent comprising a drug and an aqueous solution as described herein. In other cases, the volume comprises a first material, a second material and/or a third material wherein the first, second and/or third material is a porous material and/or a biodegradable material as described herein. Such dimensions may be expressed in a plurality of planes, including for example, but not limited to, x, y and z. As described herein, the integrally formed reservoir may comprise a plurality of volumes relative to the volume of the shell in the absence of the integrally formed reservoir. The units of volumetric measurement for the integrally formed reservoir may be cubic femtometers, picometers, nanometers, micrometers, millimeters, centimeters or the like.

The agent can be any of the agents as described herein or known to one of ordinary skill in the art. Exemplary agents include, but are not limited to, drugs, chemicals, genes, polypeptides, enzymes and the like. Agents may be in an active form or in a pre-form. For example, a pre-form agent, such as a pre-form enzyme, may be inactive towards the target and following interaction with another agent, often an enzyme such as salivary amylase, the pre-form of the inactive enzyme is digested into the active form of the enzyme. In some aspects, the agent is a medical grade drug, chemical agent, or a bioactive agent. Examples of the drug or agent can include antibacterials, antibiotics, anti-inflammatory agents, immune-suppressive agents, immune-stimulatory agents, dentinal desensitizers, odor masking agents, immune reagents, anesthetics, nutritional agents, antioxidants, lipopolysaccharide complexing agents, and peroxides, among others.

In some aspects, agents may be compounded with a pharmaceutically acceptable salt, for example, any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts. Examples of bases include, but are not limited to, alkali metal (e.g., sodium) hydroxides, alkaline earth metal (e.g., magnesium) hydroxides, ammonia, and compounds of formula $NW_4^+$, wherein W is Cm alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecyl sulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenyl propionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_1$ˆ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In some aspects, agents may be a nucleic acid molecule, for example, any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, methyladenine, I-methylpseudouracil, I-methylguanine, I-methylinosine, 2,2-di methylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, ethyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

In some aspects, agents may be a gene, for example, a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." introns are segments of a gene that are transcribed into nuclear RNA (linRNA); introns may contain regulatory elements such as enhancers. Introns are removed or "spliced Out" from the nuclear or primary transcript; introns therefore are absent in the messenger RNA (mRNA) transcript. The mRNA functions during translation to specify the sequence or order of amino acids in a nascent polypeptide.

The agent may be present in or on a carrier or binder and/or which creates a matrix from which the agent can be released by diffusion or dissolution. In some cases, the agent is dissolved in the carrier or binder. In this case, the agent may be provided in powder or similar form and dissolved in a liquid solvent. The result may be a solution which may be filled into the integrally formed reservoir through the inlet and/or universal port. When the repositioning appliance is placed over the patient's teeth, the agent may be released from the integrally formed reservoir as described herein. Release may be due to activation or deactivation of the carrier or any other releasing mechanism, such as by enzymes or proteins in saliva. Or release may be due to degradation of the carrier by contact with, for example, saliva. It may be appreciated that any agent, particularly fluoride materials, antibiotics, bleaching materials and breath fresheners, may be delivered to the oral environment in this manner.

In some cases, the carrier or a material comprising at least a portion of the integrally formed reservoir is degradable (e.g., dissolvable, biodegradable, and the like). For example, the second material, the third material and additional other materials as described herein may be degradable materials. Degradable materials for use in the systems, methods and appliances as described herein are known to those of ordinary skill in the art. Degradable materials as disclosed herein are exemplary and the systems, methods and appliances as described herein may be used in combination with any degradable material known to one of ordinary skill in the art. While not limiting, properties of degradable materials include the following examples, such as absorption of aqueous solutions (e.g., saliva, water and the like), adsorption of aqueous solutions (e.g., saliva, water and the like), pH and/or changes in pH, temperature and/or changes in temperature, enzymatic sensitivity wherein sensitivity includes the degradable material comprising enzymatic substrates, mechanical disruption and/or stimulation, electrical and/or stimulation, sonic and/or stimulation and any other methods of degradation known to one of ordinary skill in the art.

The degradation products often define the biocompatibility of a polymer. Synthetic biodegradable polymers are favored over natural ones because of reliability of raw materials. In some aspects, the degradable material may be, but is not limited to, polyglycolide (PGA), polylactide (PLA), l-lactide (LPL A), poly(dl-lactide) (DLPLA), poly (caprolactone) (PCL), polydioxanone poly(glycolide-co-trimethylene carbonate) (PGA-TMC), and polyorthoesters.

In some aspects, the material can comprise and/or the integrally formed reservoir may comprise an enzyme or a reactor that reacts with enzymes from the oral fluids. When oral fluids or enzyme from the oral fluids enters the well, the material reacts with the enzyme to provide an indication. Alternatively, a pH indicator can be used as the material. In yet another embodiment, the membrane can be silicon instead of PVS.

In another aspect, the polymer can be water-soluble polymer that includes water-soluble polymers, lightly cross-linked hydrogels, and high molecular weight with hydrogen bonding plastics that demonstrate some limited water resistance. Natural-based water-soluble polymers include starch, starch-oxided, cellulose, cellulose-alkoxylated, cellulose-carboxyalkylated, chitin, chitosan, pectins, hyaluronic acid, proteins, and lignin. Water-soluble polymers can also be created from synthetic raw material through polymerization by addition/vinyl, condensation, and ring-opening. Examples of these types of polymers are polyvinyl alcohol), polyesters, and poly(allkylene oxides). The hydrolytic instability of biodegradable polymers is advantageous because the presence of the oral fluids will facilitate the degradation of the polymer.

Figure 3D:
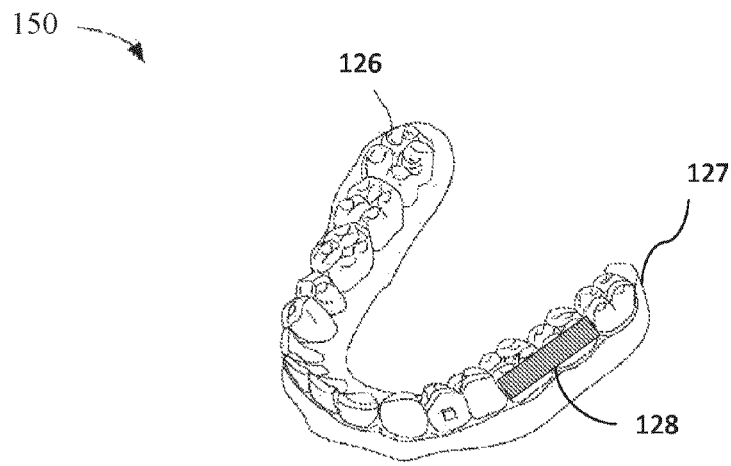
FIG. 3D illustrates a tooth receiving appliance comprising a shell with an integrally formed reservoir, the shell and the integrally formed reservoir comprising the same material in accordance with an embodiment.

In some aspects, the tooth receiving appliance is comprised of a material as disclosed herein. The integrally formed reservoir may be formed from the same material as the shell of the tooth receiving appliance. FIG. 3D illustrates a tooth receiving appliance 126 comprising a shell 127 with an integrally formed reservoir 128, the shell 127 of the tooth receiving appliance 126 fabricated from a first material and the integrally formed reservoir fabricated from the first material. Any of the appliances described herein can be designed and/or provided as part of a set of a plurality of appliances used in a tooth receiving system 150. In some cases, the material comprising the integrally formed reservoir may comprise a different porosity than the material comprising the shell. Often the integrally formed reservoir may comprise porous and non-porous material. For example, the integrally formed reservoir may be directly fabricated with the first material comprising pores. The diameter of the pores may be, but is not limited to, about 50 µm, about 30 µm, about 25 µm, about 20 µm, about 15 µm, about 10 µm, about 5 µm, about 1 µm, about 500 nm, about 100 nm, about 10 nm, or about 1 nm. In some cases, the pores of the material comprising a portion of the integrally formed reservoir may be the same size or different sizes. The porous properties of a material can be used as a method of controlling diffusion of an agent from the integrally formed reservoir. For example, larger pores, such as 50 µm may be selected as the diameter of the pores in the porous material when the agent is of a small molecular weight, thus the porous material is configured for a higher rate of diffusion of the agent through the pores and into the intraoral cavity. As another example, medium-sized pores, such as 25 µm may be selected as the diameter of the pores in the porous material when the agent is of a small molecular weight, thus the porous material is configured for a medium rate of diffusion of the agent through the pores and into the intraoral cavity. The plurality of agents described herein or others known to one of skill in the art can comprise a plurality of molecular weights. The pore sizes described herein or others known to one of ordinary skill in the art of the porous material can be selected during the methods of manufacturing and/or fabricating the shell in order to facilitate a desired rate of delivery and/or desired rate of diffusion of the agent from the integrally formed reservoir. The first material may be selected from a material as described herein or known to one of ordinary skill in the art and often, but is not limited to, lacking degradable properties.

Figure 3E:
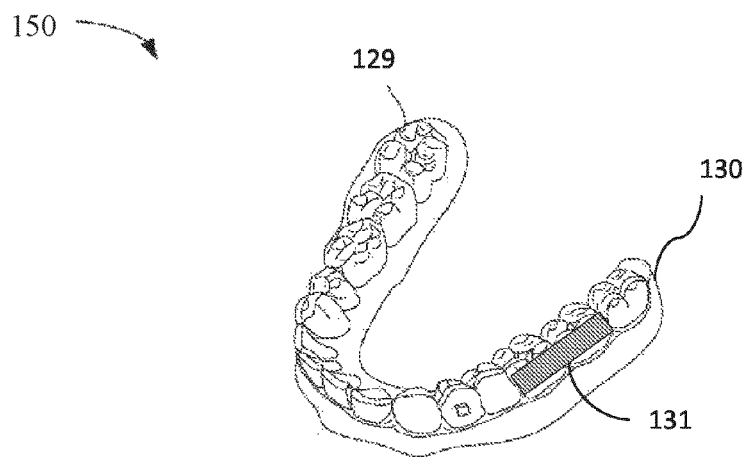
FIG. 3E illustrates a tooth receiving appliance comprising a shell with an integrally formed reservoir, the shell comprising a first material and the integrally formed reservoir comprising a second material in accordance with an embodiment.

FIG. 3E illustrates a tooth receiving appliance 129 comprising a shell 130 with an integrally formed reservoir 131, the shell 130 of the tooth receiving appliance 129 fabricated from a first material and the integrally formed reservoir fabricated from a second different material. Any of the appliances described herein can be designed and/or provided as part of a set of a plurality of appliances used in a tooth receiving system 150. In some cases, the second material comprising the integrally formed reservoir may comprise a different porosity than the material comprising the shell. Often the integrally formed reservoir may comprise porous and non-porous portions of the second material. For example, the integrally formed reservoir may be directly fabricated with the second material comprising pores. The diameter of the pores may be, but is not limited to, about 50 µm, about 30 µm, about 20 µm, about 15 µm, about 10 µm, about 5 µm, about 1 µm, about 500 nm, about 100 nm, about 10 nm, or about 1 nm. In some cases, the pores of the material comprising a portion of the integrally formed reservoir may be the same size or different sizes. The first material may be selected from a material as described herein or known to one of ordinary skill in the art and often, but is not limited to, lacking degradable properties. The second material may be selected from a material as described herein or known to one of ordinary skill in the art and often, but is not limited to, is a degradable material.

Figure 3F:
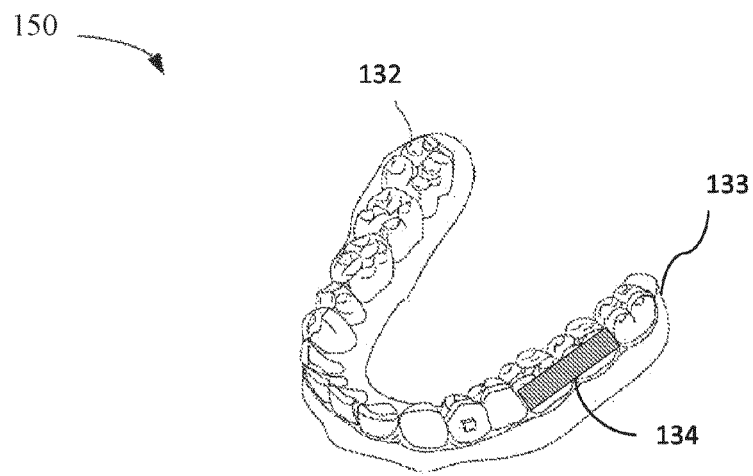
FIG. 3F illustrates a tooth receiving appliance comprising a shell with an integrally formed reservoir, the shell comprising a first material and the integrally formed reservoir comprising a first and a second material in accordance with an embodiment.

FIG. 3F illustrates a tooth receiving appliance 132 comprising a shell 133 with an integrally formed reservoir 134, the shell 133 of the tooth receiving appliance 132 fabricated from a first material. A portion of the integrally formed reservoir is fabricated from the first material and a portion of the integrally formed reservoir fabricated from a second different material. Any of the appliances described herein can be designed and/or provided as part of a set of a plurality of appliances used in a tooth receiving system 150. In some cases, the second material comprising the integrally formed reservoir may comprise a different porosity than the material comprising the shell. Often the integrally formed reservoir may comprise porous and non-porous portions of the second material. For example, the integrally formed reservoir may be directly fabricated with the second material comprising pores. The diameter of the pores may be, but is not limited to, about 50 µm, about 30 µm, about 20 µm, about 15 µm, about 10 µm, about 5 µm, about 1 µm, about 500 nm, about 100 nm, about 10 nm, or about 1 nm. In some cases, the pores of the material comprising a portion of the integrally formed reservoir may be the same size or different sizes. The first material may be selected from a material as described herein or known to one of ordinary skill in the art and often, but is not limited to, lacking degradable properties. The second material may be selected from a material as described herein or known to one of ordinary skill in the art and often, but is not limited to, is a degradable material.

Figure 3G:
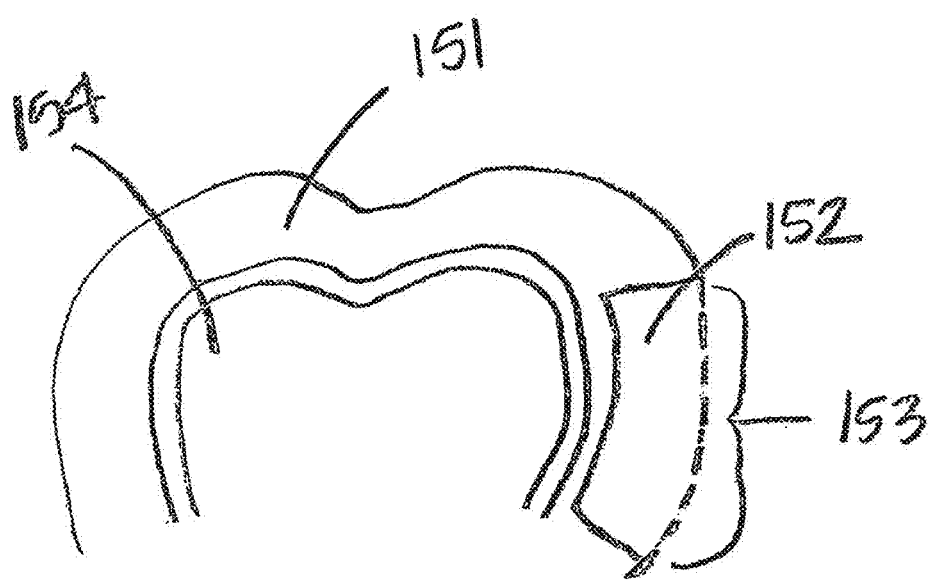
FIG. 3G illustrates a cross-section view of a shell and an integrally formed reservoir comprising a rate controlling membrane in accordance with an embodiment.

In some aspects of the embodiments described herein, a rate controlling membrane is disposed over the integrally formed reservoir and controls the rate at which the substance is released from the integrally formed reservoir. FIG. 3G illustrates a cross-section view of a shell 151 and an integrally formed reservoir 152 comprising a rate controlling membrane 153, the shell positioned around a tooth 154. The rate controlling membrane 153 may be disposed over a portion of a wall of the integrally formed reservoir, over a portion of a plurality of walls or may form a wall of the integrally formed reservoir. The depiction herein of the rate controlling membrane 153 as forming a wall of the integrally formed reservoir is exemplary and not intended to limit the relative size of the rate controlling membrane or the position of the rate controlling membrane that may be used in aspects of the embodiments described herein. The rate controlling membrane 153 may include pores to control release of an agent from the reservoir 152. The diameter of the pores may be, but is not limited to, about 50 µm, about 30 µm, about 20 µm, about 15 µm, about 10 µm, about 5 µm, about 1 µm, about 500 nm, about 100 nm, about 10 nm, or about 1 nm. In some cases, the pores of the rate controlling membrane 153 may be the same size or different sizes. The rate controlling membrane may be formed from a material as described herein or known to one of ordinary skill in the art and often, but is not limited to, includes a degradable material.

The reservoir may be pre-filled or preloaded with an agent or substance for delivery. In this case, the appliance may be ready for insertion or use upon removal from any packaging without the need of loading the appliance with the agent for delivery. If the releasing means is designed for a single delivery period, the appliance may be worn throughout the prescribed repositioning period and then disposed of. If the releasing means is designed for multiple delivery periods, the reservoir may be replenished with the agent to be released any number of times throughout the prescribed repositioning period. It may be appreciated that any agent, particularly fluoride materials, antibiotics, bleaching materials and breath fresheners, may be delivered to the oral environment in this manner.

Figure 3H:
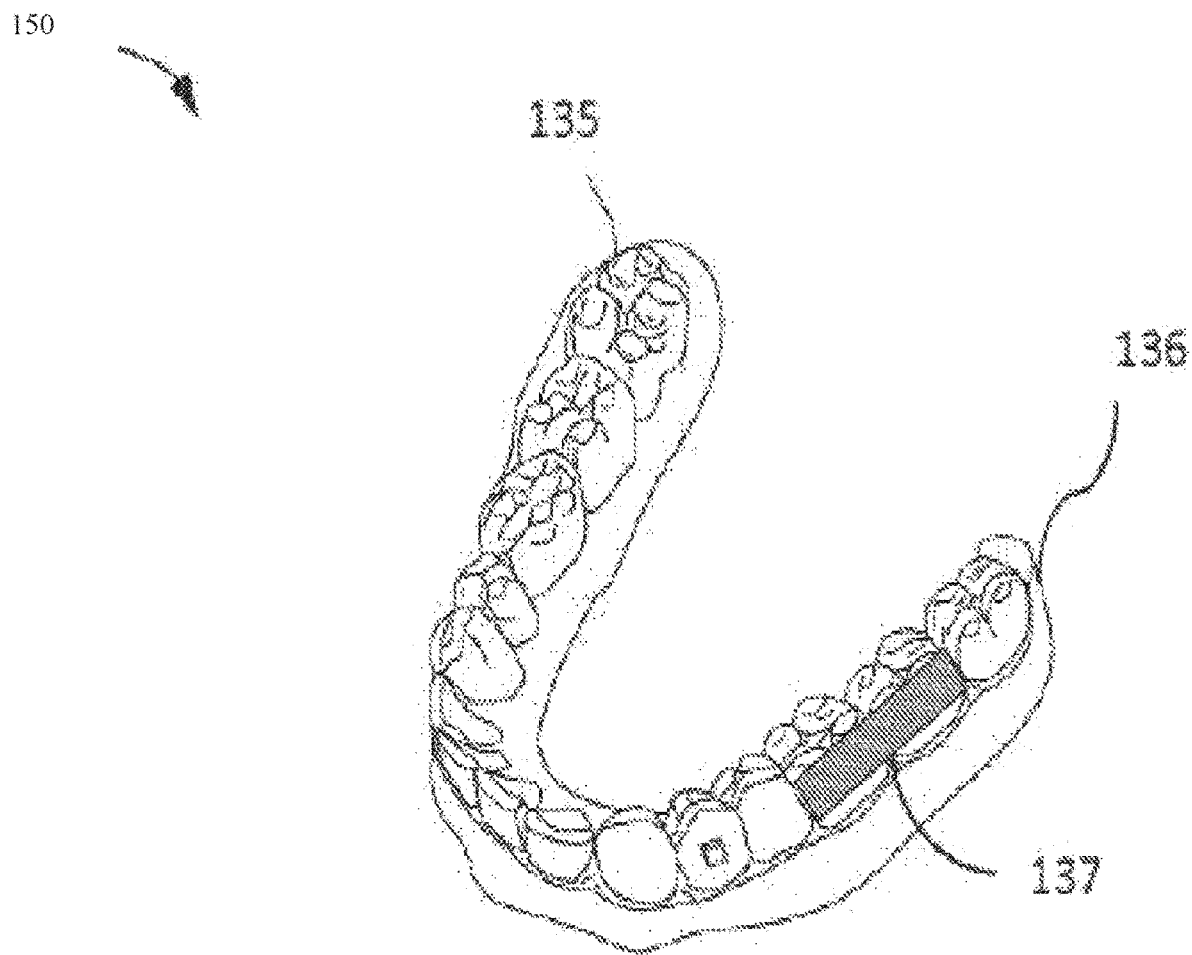
FIG. 3H illustrates a tooth receiving appliance comprising a shell with an integrally formed reservoir in accordance with an embodiment.

FIG. 3H illustrates a tooth receiving appliance 135 comprising a shell 136 with an integrally formed reservoir 137, the shell 136 of the tooth receiving appliance 135 fabricated from a first material. A portion of the integrally formed reservoir can be fabricated from a second material and a portion of the integrally formed reservoir can be fabricated from a third material. Any of the appliances described herein can be designed and/or provided as part of a set of a plurality of appliances used in a tooth receiving system 150. The first material may be selected from a material as described herein or known to one of ordinary skill in the art and often, but is not limited to, lacking degradable properties. The second material may be selected from a material as described herein or known to one of ordinary skill in the art and often, but is not limited to, is a degradable material. The third material may be selected from a material as described herein or known to one of ordinary skill in the art and often, but is not limited to, is a degradable material.

Kinetics of agent release may be affected by the material and other features of the tooth receiving appliance. For example, the material comprising the shell may affect the response of the shell to a stimulus. Features of the material that may affect the response to the stimulus include the polymer length, crosslinking, presence of other molecules within the polymers of the shell, flexibility of the shell under various conditions (e.g., temperature changes, pH changes). Additional features which may affect agent release kinetics may include, but are not limited to, the pharmaceutical carrier, the tooth receiving appliance geometry, stimulus, materials comprising the reservoir, pores within the materials comprising the reservoir, mechanism of biodegradation, etc.

Flexible shape change from a first shape where the agent is stored within the reservoir and the port (e.g., outlet or universal port) is in a closed position, to a second shape formed in response to a stimulus (e.g., pressure, pH, temperature, and other stimuli described herein or known to a person of ordinary skill in the art) to the tooth receiving appliance, the stimulus inducing opening of the port (e.g., outlet or universal), the agent stored within the reservoir is released from the reservoir through the port, and then to a third shape when the stimulus is removed from the tooth receiving appliance, the port returns to a closed position and the reservoir contains less agent in the third shape than the reservoir contained in the first shape. Stimulus-induced release of the agent stored within the reservoir in the second shape may induce release of various amounts of the agent stored within the reservoir. For example, the stimulus may induce release of the entirety of the agent stored within the reservoir or a portion of the agent stored within the reservoir. The amount of agent released may be affected by various factors, including but not limited to, the amount or degree of stimulus (e.g., magnitude of pressure, change in pH, change in temperature, or other amounts or degrees known to a person of ordinary skill in the art), the duration of the stimulus (e.g., amount of time the stimulus is applied), the size of the port, whether the port is connected to a channel and the structure of the channel (e.g., straight, curved, multiples of various planes), the pharmaceutical carrier in which the agent is compounded, the viscosity and/or density of the carrier, kinetics of the agent or other factors known to a person of ordinary skill in the art.

In some aspects of the embodiments, the integrally formed reservoir may be located in a plurality of positions within the aligner shell. The location of the integrally formed reservoir may be determined during the methods of planning a patient's treatment plan, during the fabrication step or any other method described herein. In some cases, the placement of the integrally formed reservoir depends upon the agent to be released from the integrally formed reservoir, such agents as discussed herein or known to one of ordinary skill in the art. In some cases, the placement of the integrally formed reservoir depends upon the material from which the formed reservoir is comprised, such materials as discussed herein or known to one of ordinary skill in the art. In some aspects, the shell can contain one or more walls defining teeth receiving cavities (occlusal, buccal, and/or lingual walls) and the reservoir can be formed partially or wholly within the wall(s). The plurality of positions may include, but is not limited to, the lingual surface, the occlusal surface, the buccal surface, the gingival portion, the interior surface (e.g., near the received teeth), the exterior surface (e.g., away from the received teeth), the anterior portion, the posterior portion, the distal portion, the mesial portion or the like, or combinations thereof. The integrally formed reservoir may be positioned such that the longest axis of the integrally formed reservoir aligns with or does not align with the mesial-distal axis of the shell. The integrally formed reservoir may be positioned such that the longest axis of the integrally formed reservoir aligns with or does not align with the posterior-anterior axis of the shell. The integrally formed reservoir may be positioned such that the longest axis of the integrally formed reservoir aligns with or does not align with the posterior-anterior axis of the shell. The integrally formed reservoir may be positioned such that the longest axis of the integrally formed reservoir aligns with or does not align with the vertical axis of the shell. In some aspects, a shell can contain one or more walls defining teeth receiving cavities (occlusal, buccal, and/or lingual walls) and the reservoir can be formed partially or wholly within the wall(s). In some aspects, placement of the reservoir within the shell, as described herein, may affect the response of the shell to the stimulus. For example, the reservoir can be positioned near an area of the intraoral cavity where localized drug delivery is desired.

Some embodiments described herein include an aligner shell comprising an integrally formed reservoir configured to receive, store and release an agent. In some cases, the aligner may be supplied to the patient with the integrally formed reservoir prefilled with the agent. In other cases, the aligner may be supplied to the patient without the agent prefilled into integrally formed reservoir. In such cases, the reservoir is filled with the agent at some time point after receipt of the aligner. In any of the previous cases, the integrally formed reservoir may be refilled with an agent, either the same agent as the aligner was supplied with or a different agent, following application of the appliance to the patient's teeth. Any of the agents described herein may be prefilled, filled following receipt or refilled into the integrally formed reservoir of the aligner shell.

In some cases, the patient can wear each appliance until the agent stored within the reservoir of each appliance on the teeth has been expelled such that the reservoir no longer contains an effective amount of the agent or until the optional tooth movement can no longer be felt or until the maximum amount of expressed tooth movement for that given stage has been achieved. As described further herein, the reservoir may be filled with an agent prior to the patient receiving the appliance, or the reservoir may require filling with an agent after the patient receives the appliance. In some cases, the agent may be refilled into the reservoir during the course of treatment with said appliance. A plurality of different appliances (e.g., a set) can be designed and even fabricated prior to the patient wearing any appliance of the plurality.

In some embodiments, a polymeric shell appliance can be formed from a sheet of multiple suitable layers of polymeric material. For example, FIG. 3A shows a portion of a dental appliance 300 formed from a multi-layer polymer sheet, in accordance with an embodiment. Sometimes during orthodontic treatment, it may be necessary to apply forces to a tooth to generate movement of the tooth to, for example, bring the patient's teeth into a better occlusion in a mesial or distal direction. Mulitlayer aligners can, for example, provide increased durability of the aligners so that they can better withstand wear due to aligner reinsertion and removal and other mechanical stresses put on the aligner during treatment. In addition, multi-layer aligners have improved elastic properties that allow for less degradation in the shape of the teeth receiving cavities during a stage of treatment.

As noted above, an embodiment utilizes a multilayer sheet for use in a dental appliance. The multilayer sheet can include three layers, in which a hard polymer layer is disposed between two soft polymer layers. The sheet can include a hard polymer layer disposed between at least one first soft polymer layer and at least one second soft polymer layer. The multilayer sheets can be used in making dental aligners having improved durability for use, e.g., to the elastic properties of the multilayer sheet when formed into an aligner. In addition, the bonding strength between the layers further improves the durability of the aligners, for example, by withstanding teeth grinding by a patient.

According to the embodiment illustrated in FIGS. 3A and 3B, the appliance 300 is formed from a sheet 330 including multiple layers of polymeric material. As will be explained in more detail below, each layer can have its own associated color property such that directing certain types of energy at portions of the appliance 300 extracts and reveals the associated color in those portions. An etching device (e.g., laser or milling tool), heat, or other energy can be used to extract the color properties associated with each layer.

FIG. 3B is a side cross-sectional view of a multi-layer sheet 330 that can be used to make the multi-layer dental appliance 300. As shown, a multi-layer sheet 330 can include a three layer structure: a hard polymer layer 334 and two soft polymer layers 332, 336. The hard polymer layer 334 can be positioned between a first soft polymer layer 332 and a second soft polymer layer 336, as shown in FIG. 3B. In some embodiments, the hard polymer layer can be thicker than either of the soft polymer layers. The soft polymer layers can have the same or different thicknesses. For example, the hard polymer layer can have a thickness in a range from about 400 µm to about 1100 µm, about 450 µm to about 1000 µm, about 500 µm to about 900 µm, or about 550 µm to about 750 µm. The soft polymer layers can have a thickness in a range from about 25 µm to about 100 µm, about 30 µm to about 90 µm, or about 35 µm to about 80 µm. Multilayer sheets used for making appliances having a hard polymer layer disposed between two soft polymer layers can range from a thickness of about 500 µm to about 1200 µm, about 550 µm to about 1100 µm, or about 600 µm to about 1000 µm. In some embodiments, the thicknesses of the various layers can be tailored for a particular stage of treatment for the patient.

Suitable polymeric materials for the hard polymer layer can include a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate or a combination thereof (e.g., a blend of at least two of the listed hard polymeric materials). In some embodiments, the hard polymer layer of the appliances can include polymeric materials, such as a polycarbonate, a co-polyester, a polyester, and a thermoplastic polyurethane. In some embodiments, the hard layer can be composed of multiple hard layers, e.g., two or three hard polymer layers co-extruded to form one hard layer. According to an embodiment, a thicker polymer layer includes multiple layers with varying properties and color elements, and a thinner layer is a clear coat(s) over the thicker layer.

Suitable polymeric materials for the soft polymer layers 332, 336 of the appliance 300 can include a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, or a combination thereof (e.g., a blend of at least two of the listed soft polymeric materials). The soft polymer layers 332, 336 can either be the same material or different materials. In certain embodiments, the first soft polymer layer 332 and the second soft polymer layer 336 are the same polymeric material.

As described herein, the multi-layer sheet can include a hard polymer layer disposed between two soft polymer layers. In one embodiment, the multilayer appliance 300 can include a hard polymer layer of one type of material (e.g., a co-polyester), and two soft polymer layers of other types of material that can be the same or different (e.g., two soft polymer layers of thermoplastic polyurethane elastomer). In some embodiments, the multilayer appliances can also include a hard polymer layer of at least two layers of polymer material. For example, the hard polymer layer can include several polymer layers laminated together to form the hard polymer layer. The laminated hard polymer layer can include at least two layers of any combination of the following polymer materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and a polytrimethylene terephthalate. Similarly, in some embodiments, the multilayer appliances can include a soft polymer layer of at least two layers of polymer material. For example, the soft polymer layers can include a layer of several polymer layers laminated together. The laminated soft polymer layers can include at least two layers of any combination of the following polymer materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and a thermoplastic polyamide elastomer.

As shown in FIG. 3B, each of the soft and hard polymer layers can be formed from more than one layer or a thermal set. The first soft polymer layer 332 can be formed from three layers 332a, 332b, 332c of a soft polymer material. Similarly, the second soft polymer layer 336 can be formed from three layers 336a, 336b, 336c of either the same or a different soft polymer material. In the illustrated embodiment, the hard polymer layer 334 is also formed from three layers 334a, 334b, 334c of a hard polymer material. It will be understood that, in other embodiments, the polymer layers 332, 334, 336 can be formed from more or fewer layers. For example, the first polymer layer 332 could be formed from a single layer of a soft polymer material in one embodiment, whereas in another embodiment, the first polymer layer 332 is formed from five layers of a soft polymer material.

Each of the different layers in the appliance 300 can be associated with a different color such that when a particular layer of the appliance 300 is exposed, its associated color is also revealed in the exposed area. An example will be described below with reference to FIGS. 3A and 3B. As shown in FIG. 3A, in the illustrated embodiment, the ornamental design 310 has nine different sections 320a-320i, each having a different color. The color of each of the nine sections 320a-320i is determined by the associated layer that is exposed. For example, the top-most layer 332a could be red in this example. If the appliance 300 is fabricated and it does not have an intended ornamental design, the appliance 300 could be left as is and the entire appliance 300 could be red.

However, if an ornamental design 310 on the appliance 300 is desired, certain layers in certain portions could be removed to form the design 310. For example, section 320a could be associated with the top-most layer 332a, and therefore section 320a would be red in this example. Section 320b could be associated with the next layer 332b, which is orange in this example. To make section 320b orange, the portion of the layer above (i.e., 332a) in the area of section 320b would be removed to expose layer 332b in the area of section 320b. The thickness of the appliance depends on the intended purpose of the appliance. For example, the appliance is generally thicker if the appliance is intended to move teeth than if the appliance is intended to retain teeth or protect teeth (as a mouth guard). Typically, an orthodontic appliance has a thickness in a range of about 250 µm-2 mm. Thus, layers can be removed in the design area to expose colored layers provided the thickness of the appliance in the area is at least about 250 µm.

According to another embodiment, an ornamental design 310 can be printed on one of the layers 332, 334, 336 before the multilayer polymer sheet 330 is formed. In some embodiments, the design 310 can be an ink jet design, which adheres to the surface of the appliance 300. The multilayer sheet 330 is then formed into a dental appliance by thermoforming, as described in more detail below with reference to FIGS. 5 and 6. Alternatively, the appliance 300 can be formed by thermoforming one layer at a time. A design or portion of the design 310 can be etched in each layer before the subsequent layer is thermoformed.

In yet another embodiment, colored pellets, ink, or dye can be included in the material of the appliance 300 and light energy is used to activate certain colors to form the design 310. The colored pellets, ink, or dye can be integrated with either a single layer polymer sheet or in a multilayer sheet. Laser energy directed at the areas of the appliance 300 at a particular wavelength reacts with the colored pellets, ink, or dye to activate the colors. Laser marking of polymer material of the appliance 300 relies on carbonization or foaming processes caused by laser beam absorption. Carbonization, which is a thermochemical process, produces dark marks, whereas foaming, which is a partial degradation creating gas-bubbles within the material, scatters the light and produces light marks. Additives can help improve absorption properties. Applicable laser sources are Nd: YAG-, Nd: Vanadate- or fiber lasers. Furthermore, harmonic wavelengths of 532 nm (green) and 355 nm (UV) can be used for bleaching and photo reduction processes. UV-induced photo reduction is often called "cold marking", as there is no noticeable heating of the material. Additives in plastics can increase the diversity of colors produced by the laser process.

Permanent change thermochromic ink can be included in the polymeric material of the appliance 300, as it is a high temperature activated, permanent change ink or pigment. The permanent change thermochromic ink can produce a gradual color change that becomes denser as the temperature increases. Such permanent change thermochromic inks are manufactured by LCR Hallcrest LLC of Glenview, IL Permanent change thermochromic inks are typically activated in the range of 60 to 200° C. Numerous custom colors and temperature activation points are available for these inks.

Multilayer sheets can provide a variety of improved properties for aligners used in orthodontic treatment. As further described herein, the multilayer sheets formed into aligners can, for example, provide increased durability of the aligners so that they can better withstand wear due to teeth grinding and other mechanical stresses put on the aligner during treatment. In addition, the aligners have improved elastic properties that allow for less degradation in the shape of the teeth receiving cavities during a stage of treatment. For example, during a multistage orthodontic treatment, the capability of an aligner to force tooth movement can degrade and may cause the treatment to include more aligners to reach a final ideal arrangement and/or result in a mid-course correction that could be prevented by using aligners with improved physical properties, such as those provided herein.

Figure 4A:
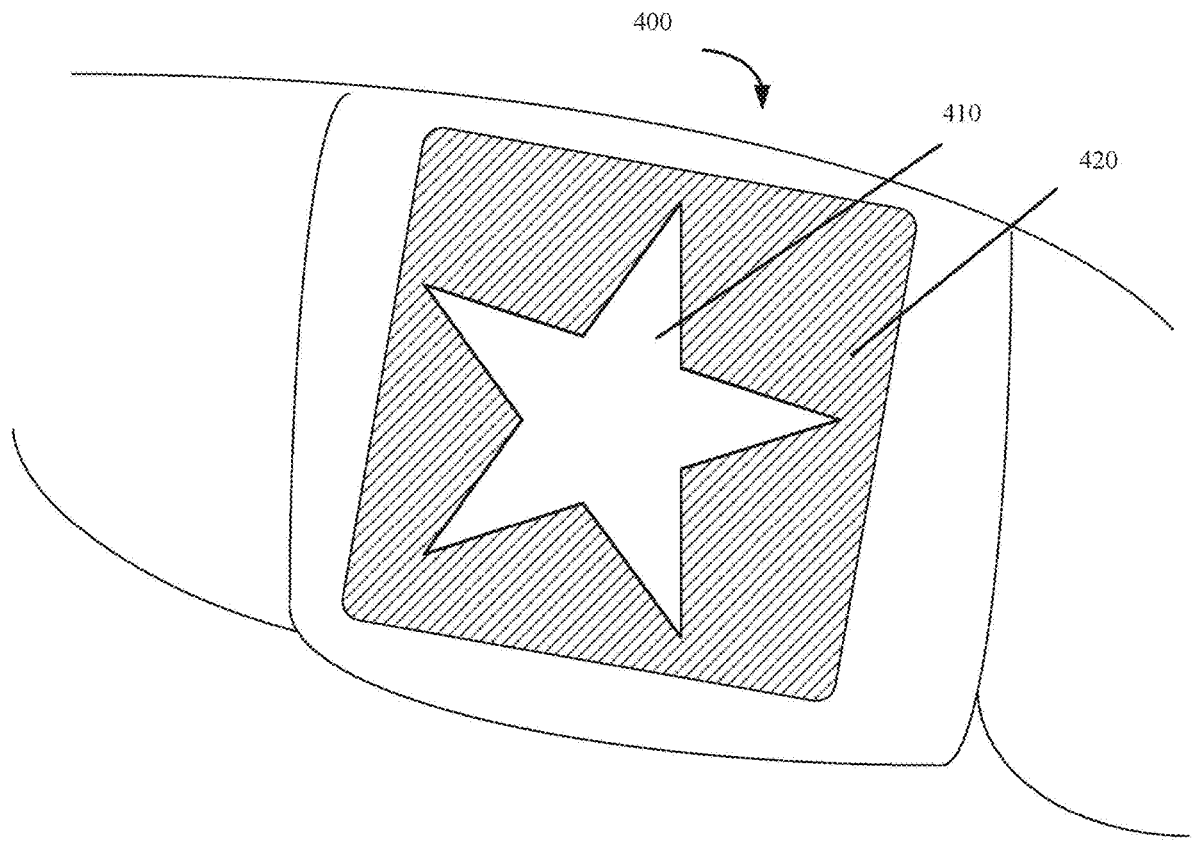
FIG. 4A is a front view of a dental appliance having an ornamental design mechanically attached in accordance with an embodiment.
Figure 4B:
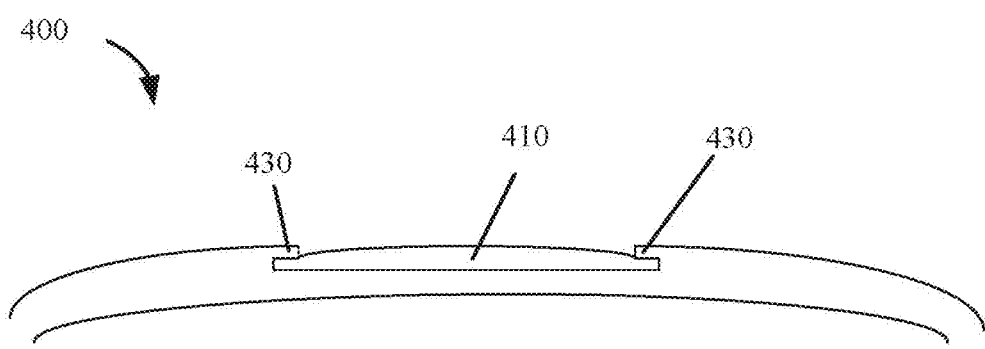
FIG. 4B is a side view of a dental appliance having an ornamental design mechanically attached in accordance with an embodiment.

Yet another embodiment will be described with reference to FIGS. 4A and 4B. FIGS. 4A and 4B show a dental appliance 400 that has an interchangeable ornamental design 410 that can be mechanically attached to the appliance 400.

In these embodiments, the mechanical attachment of the design 410 is created by first providing an indentation or recessed portion 420 on the front surface of the appliance 400. The recessed portion 420 can have a depth in the range of about 50 μm-1 mm, depending on the type of mechanical attachment. The ornamental design 410 can be attached to the front surface of the appliance 400 in the recessed portion 420. In the embodiment shown in FIG. 4A, the appliance 400 has a simple recessed portion 420 in which to receive an ornamental design 410.

In the embodiment shown in FIG. 4B, the ornamental design 410 is inserted into a recessed portion and held in place by tabs 430 which are integrally formed with the appliance 400. As shown in FIG. 4B, the ornamental design 410 is shaped such that there is a fairly smooth transition between the appliance 400 and the mechanically attached ornamental design 410 and that the design 410 is substantially flush with the surface of the appliance 400 when the design 410 is inserted into the recessed portion.

Attachment can be made by medical grade adhesive. For an ornamental design 410 attached using medical grade adhesive, the recessed portion 420 can have a depth in the range of about 50-100 μm to accommodate an adhesive sticker having about the same thickness. For an ornamental design 410 that is rigid, the recessed portion 420 can have a depth in the range of about 0.1-1 mm to accommodate the thickness of the rigid ornamental design 410. As the ornamental design 410 is mechanically attached to the appliance 400, it can be changed as desired by the patient. The ornamental design 410 does not affect the functionality of the appliance 400. However, the material of the ornamental design 410 should have sufficient flexibility to be able to flex with the appliance 400.

Figure 5:
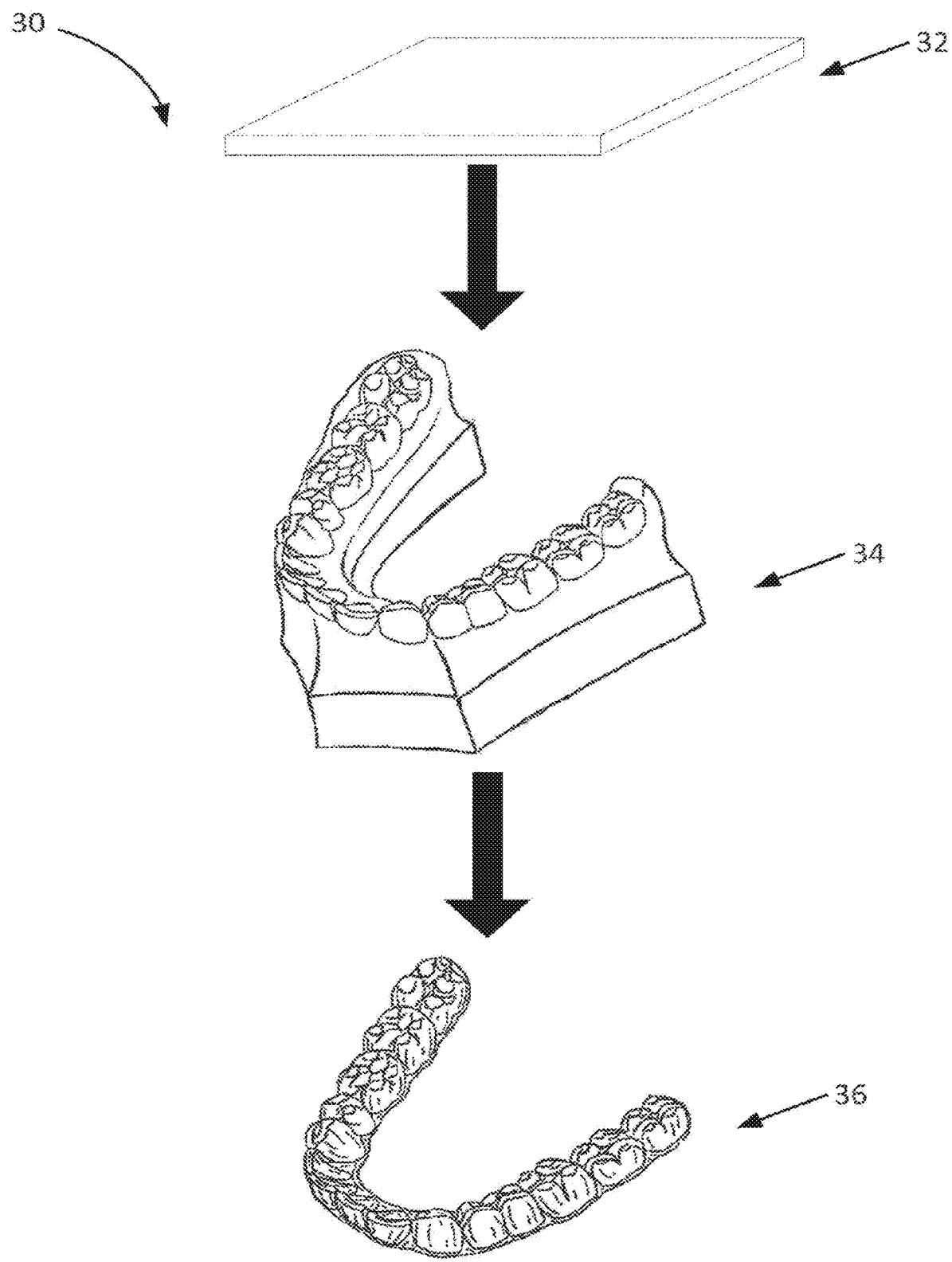
FIG. 5 depicts a process for fabricating a dental appliance in accordance with an embodiment.

FIG. 5 depicts an example embodiment of a process 30 for forming a dental appliance, in accordance with an embodiment. As shown, a polymer sheet 32 can be formed into a tooth positioning appliance 36. In some embodiments, the polymer sheet 32 can be a multilayer sheet, such as the multilayer sheet 330 described above. As noted above, a multilayer polymer sheet can a hard polymer layer disposed between two soft polymer layers.

In this exemplary process, the dental appliance 36 can be produced with the use of a physical tooth model, or mold, 34. The dental appliance 36 can be produced by heating the thermoformable polymer sheet 32 and then vacuum or pressure forming the sheet over the teeth in the physical tooth model 34. The dental appliance 36 is a direct representation of the physical tooth model. Excess material from the sheet can be trimmed to form a final dental appliance that can be used for dental/orthodontic treatment of a patient.

One or a series of physical tooth models, such as the model described above, may be used in the generation of elastic repositioning appliances for orthodontic treatment. Similar to the process above, each of the appliances can be generated by thermoforming a polymeric material over a mold of a desired tooth arrangement to form a dental appliance. The tooth positioning appliance of the desired tooth arrangement generally conforms to a patient's teeth, but is slightly out of alignment with the initial tooth configuration. Placement of the elastic positioner over the patient's teeth applies controlled forces in specific locations to gradually move the teeth into the desired configuration. Repetition of this process with successive appliances comprising new configurations eventually moves the teeth through a series of intermediate configurations to a final desired configuration.

Figure 6:
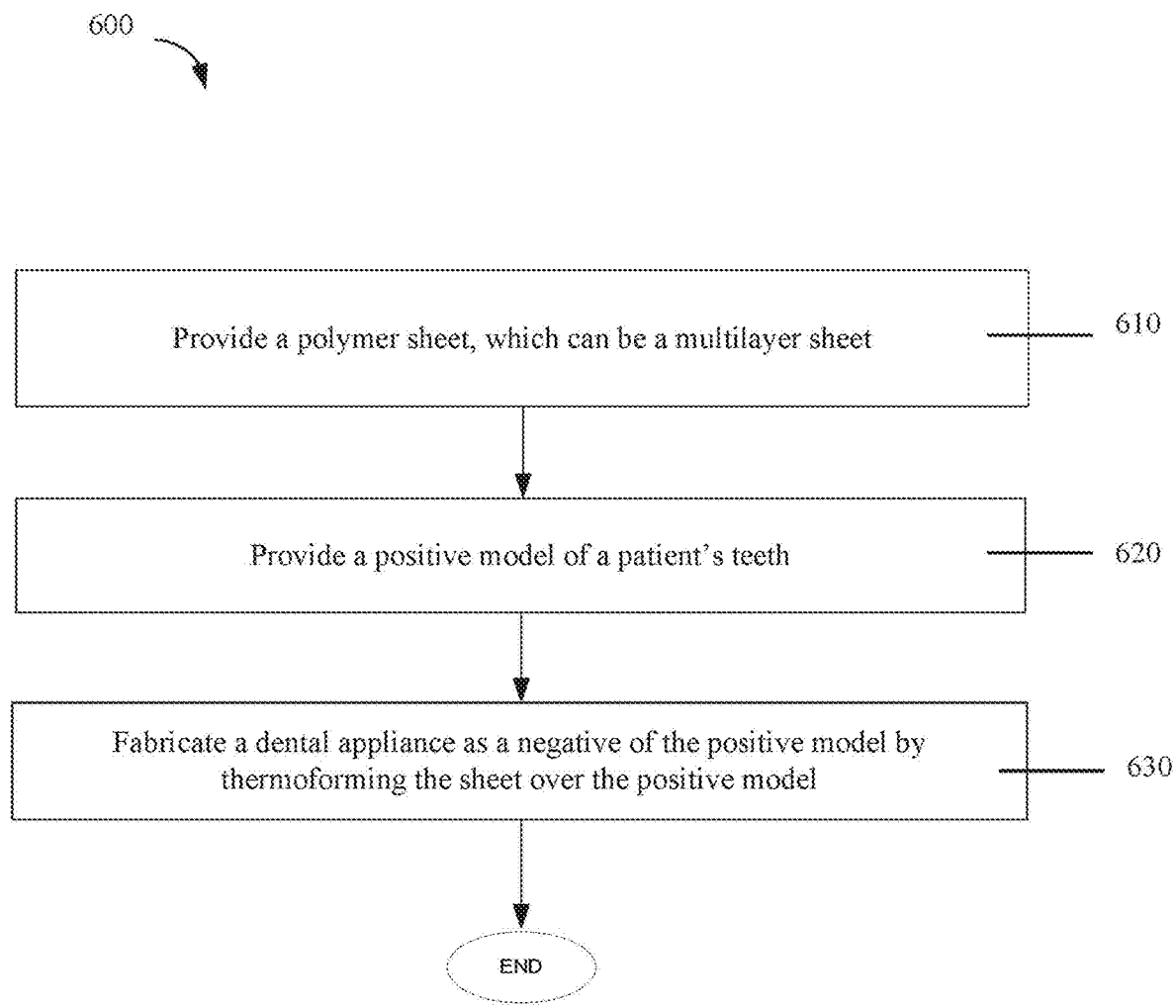
FIG. 6 is a flow chart of a process for fabricating a dental appliance in accordance with an embodiment.

FIG. 6 shows a simple schematic for a method 600 of fabricating a removable orthodontic tooth positioning appliance having teeth receiving cavities shaped to directly receive at least some of the patient's teeth and apply a resilient positioning force to the patient's teeth, in accordance with an embodiment. The method can include providing a polymer sheet, which can be a multilayer sheet having a hard polymer layer disposed between two soft polymer layers in step 610. The method can further include providing a positive physical model of a patient's teeth in step 620. The tooth positioning appliance can be fabricated by thermoforming the polymer sheet over the positive physical model in step 630, in which the tooth positioning appliance is a negative of the positive model. As described above, the method 600 of fabrication can further include trimming or cutting portions of the sheet to render a final, usable appliance for dental or orthodontic treatment.

Although fabricating an appliance by thermoforming is described with reference to FIGS. 5 and 6, it will be appreciated that a variety of methods can be used for fabricating the dental appliances described herein. As noted above, the appliances can be fabricated by thermoforming, milling, 3D printing, stereolithography, casting, etc. Some embodiments of the orthodontic appliances herein (or portions thereof) can be produced using direct fabrication, such as additive manufacturing or rapid prototyping techniques. Layers and thickness can be added to desired regions by printing, spraying, painting, and dipping the aligner.

In many embodiments, stereolithography involves selective polymerization of a photosensitive resin (e.g., photopolymer) according to a desired cross-sectional shape using light (e.g., ultraviolet light). The object geometry can be built up in a layer-by-layer fashion by sequentially polymerizing a plurality of object cross-sections. As another example, the appliances herein can be fabricated using selective laser sintering. In many embodiments, selective laser sintering involves using a laser beam to selectively melt and fuse a layer of powdered material according to a desired cross-sectional shape in order to build up the object geometry. As yet another example, the appliances herein can be fabricated by fused deposition modeling. In many embodiments, fused deposition modeling involves melting and selectively depositing a thin filament of thermoplastic polymer in a layer-by-layer manner in order to form an object. In yet another example, 3D printing can be used to fabricate the appliances herein. In many embodiments, 3D printing involves jetting or extruding one or more materials onto a build surface in order to form successive layers of the object geometry. For example, a 3D printer can be used to print the ornamental design. One or more colors can be printed on the appliance to form the design as the appliance is printed using a 3D printer.

In many embodiments, the direct fabrication methods provided herein build up the object geometry in a layer-by-layer fashion, with successive layers being formed in discrete build steps. Alternatively or in combination, direct fabrication methods that allow for continuous build-up of an object geometry can be used, referred to herein as "continuous direct fabrication." Various types of continuous direct fabrication methods can be used. As an example, in many embodiments, the appliances herein are fabricated using "continuous liquid interphase printing," in which an object is continuously built up from a reservoir of photopolymerizable resin by forming a gradient of partially cured resin between the building surface of the object and a polymerization-inhibited "dead zone." In many embodiments, a semi-permeable membrane is used to control transport of a photopolymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, the disclosures of each of which are incorporated herein by reference in their entirety.

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing") or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

The direct fabrication approaches provided herein are compatible with a wide variety of materials. The properties of the materials used can be selected according to the desired properties for the corresponding portions of the appliance. Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step. For instance, a multi-tip extrusion apparatus can be used to selectively dispense multiple types of materials from distinct material supply sources in order to fabricate an object from a plurality of different materials. Such methods are described in U.S. Pat. No. 6,749,414, the disclosure of which is incorporated herein by reference in its entirety. Alternatively or in combination, a multi-material direct fabrication method can involve forming an object from multiple materials in a plurality of sequential manufacturing steps. For instance, a first portion of the object (e.g., an appliance shell) can be formed from a first material in accordance with any of the direct fabrication methods herein, then a second portion of the object (e.g., one or more elastics) can be formed from a second material in accordance with methods herein, and so on, until the entirety of the object has been formed.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness. In many embodiments, direct fabrication allows for the entirety of the appliance (e.g., shell, discontinuities, elastics, and/or other auxiliary components) to be integrally produced in a single step, thus obviating the need for additional steps, e.g., to form a discontinuity in the shell and/or couple an elastic or an auxiliary component to the shell. For example, using direct fabrication techniques, various types of discontinuities (e.g., cuts, flaps, apertures, deformations, etc.) can be formed concurrently with the forming of the appliance shell, rather than being formed in a separate material removal step. This approach can advantageously improve the accuracy and fidelity with which the discontinuity is formed, as well as avoid the possibility of damage to the appliance shell by the material removal process.

Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). Any of the structures described herein (e.g., reservoir, ports, pores, channels, etc.) can be easily fabricated as integrally formed structures within the appliance using the methods described herein (e.g., direct fabrication). For example, in some embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm.

The direct fabrication techniques described herein can be used to produce appliances with substantially isotropic material properties, e.g., substantially the same or similar strengths along all directions. In some embodiments, the direct fabrication approaches herein permit production of an orthodontic appliance with a strength that varies by no more than about 25%, about 20%, about 15%, about 10%, about 5%, about 1%, or about 0.5% along all directions. Additionally, the direct fabrication approaches herein can be used to produce orthodontic appliances at a faster speed compared to other manufacturing techniques. In some embodiments, the direct fabrication approaches herein allow for production of an orthodontic appliance in a time interval less than or equal to about 1 hour, about 30 minutes, about 25 minutes, about 20 minutes, about 15 minutes, about 10 minutes, about 5 minutes, about 4 minutes, about 3 minutes, about 2 minutes, about 1 minutes, or about 30 seconds. Such manufacturing speeds allow for rapid "chair-side" production of customized appliances, e.g., during a routine appointment or checkup.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

In one embodiment, direct fabrication (e.g., 3D printing) is used to pattern an ornamental design, layer by layer, using a colored material that is different from the material used for the rest of the aligner structure. According to another embodiment, direct fabrication (e.g., 3D printing) is used to create, layer by layer, a cavity or reservoir in the aligner in the shape of a pattern that can be filled with either a colored liquid (e.g., medical grade substance, compliance indicator substance, or medicine) or a colored direct fabrication resin using a 3D printing technique (e.g., stereolithography, photolithography, sintering, etc.). In an embodiment, the colored liquid or resin can be added after fabrication of the shell appliance and sealed to form the ornamental design.

An integrally formed reservoir or cavity may further include features for receiving and releasing an agent. In the embodiment shown in FIGS. 7A-7D, a cavity or reservoir 710 is formed, using a direct fabrication technique, near the exterior surface of a shell appliance 700. The cavity 710 is provided with a feed channel 720 extending to the exterior surface of the appliance 700. After direct fabrication of the shell appliance 700, the cavity 710 is filled through the feed channel 720 with a biocompatible colored liquid or resin having a suitable viscosity. In some embodiments, the liquid or resin is curable. In addition to the feed channel 720, a vent 730 is also provided to allow uncured liquid or resin to drain, and also to allow air to escape while the colored liquid or resin is injected into the cavity 710 through the feed channel 720.

Figure 7A:
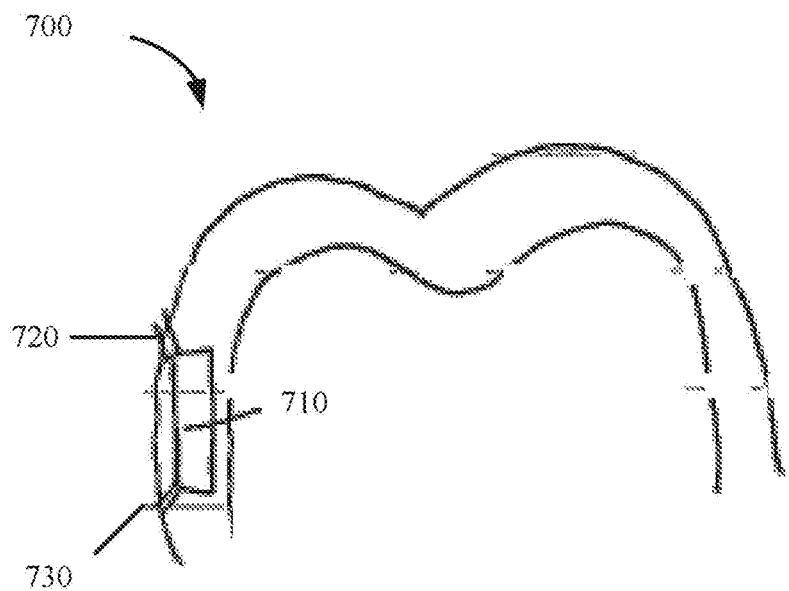
FIGS. 7A-7D show an embodiment of a dental appliance having an ornamental design formed using direct fabrication.
Figure 7B:
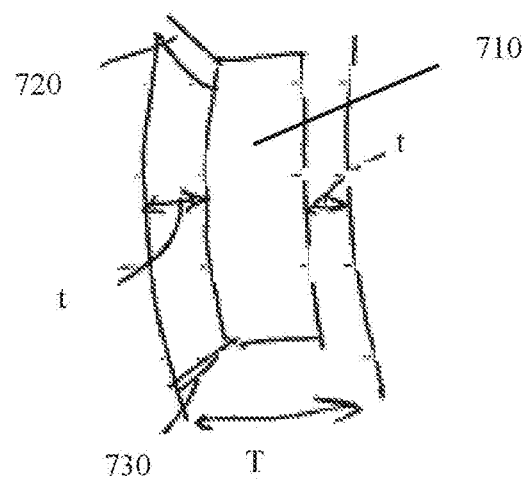

Typically, the appliance 700 has a thickness T of about 0.5 mm. In the illustrated embodiment, as shown in FIG. 7B, the appliance has a thickness t of about 50-100 µm in front of and behind the cavity 710. According to an embodiment, the feed channel 720 and the vent each has a diameter in a range of about 50-100 µm. The cavity 710, which can be shaped in an ornamental pattern or design, can have channels having a width in a range of about 50 µm-5 mm and a depth of about 100-200 µm.

Figure 7C:
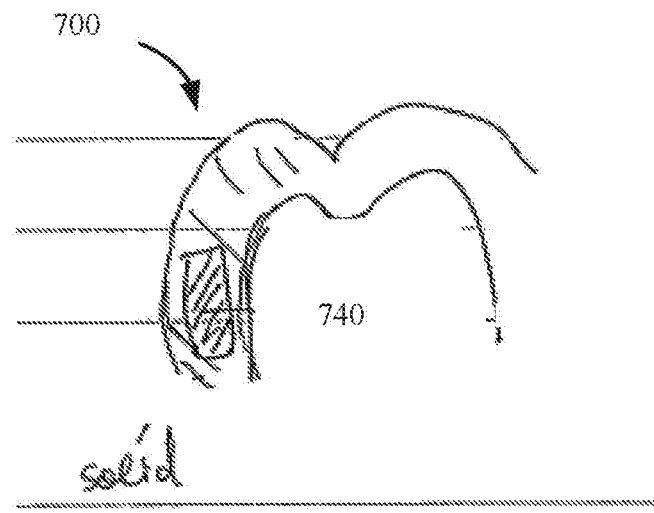
Figure 7D:
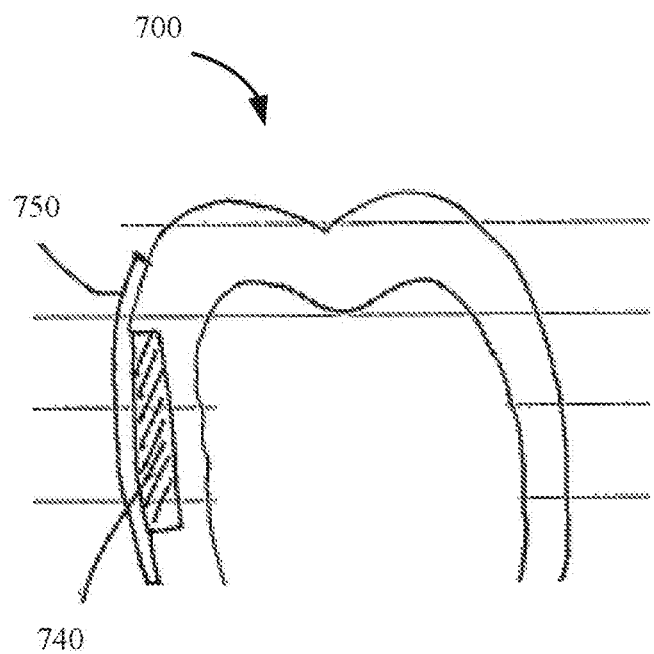

As shown in FIG. 7C, the colored liquid or resin can be cured in the cavity 710 to solidify the ornamental design 740 in the cavity 710 such that the ornamental design 740 is solid like the appliance 700. After the liquid or resin is cured, a clear coating or layer 750 is applied to seal it within the cavity 710 in the shell appliance 700, as shown in FIG. 7D. The clear coating or layer 750 can be sprayed or deposited to cover the openings of the feed channel 720 and the vent 730 to seal the liquid or resin within the cavity 710. It will be understood that the feed channel 720 and vent 730 can be provided at any suitable location on the cavity 710.

Alternatively, in another embodiment, the colored liquid (such as a compliance indicator substance or medicine) can be allowed to dissipate through a hole in the appliance portion covering the cavity. The hole opens due to heat when the shell appliance is placed in a patient's mouth. In another embodiment, the colored liquid can be allowed to dissipate or chemically change colors due to the interaction or saliva, light, and/or heat over time to indicate compliance. According to yet another embodiment, direct fabrication (e.g., 3D printing) is used to create a pattern on the outside or inside of the aligner so that the pattern can be painted to create an ornamental design.

A channel may also be integrally formed into the shell of the appliance. Integral formation of channels can be performed by direct fabrication as described herein. In some aspects of the embodiments, a channel may be operably connected to an integrally formed reservoir. In some aspects of the embodiments, a channel may have a plurality of geometries including shapes, dimensions, angles and the like. Shapes of a x-axial cross section or a y-axial cross section of the integrally formed channel include, but are not limited to, a circle, an oval, an ellipse, a curved structure with a complex shape, a triangle, a square, a rectangle, a triangle, a polygon, a pentagon, a hexagon, a heptagon, and the like. The integrally formed channel may have walls which are straight or curved, as such, the walls of the integrally formed channel may or may not form angles. The integrally formed channel may have a path within the aligner shell. For example, a path of the channel includes the distance and direction of the channel from the outlet port or universal port of the integrally formed reservoir to the channel outlet port. In some aspects, the channel has a plurality of outlet ports, and in these aspects, the path includes the distance and direction of the channel from the outlet port or universal port of the integrally formed reservoir to each of the plurality of the channel outlet ports. The path of the channel includes at least one segment and may include a plurality of segments. For example, at least one segment may be a straight or a curved path between the outlet port or the universal port of the integrally formed reservoir. The segments may have any of a plurality of geometries as described herein or known to one of ordinary skill in the art. Segment geometries include, but are not limited to, straight, curve, arc, angle, turn, spiral, circle, elbow, hairpin and the like. Segment geometries may distribute through a single plane (e.g., x-axis, y-axis, z-axis) of the shell or may distribute through a plurality of planes through the aligner shell. A person of ordinary skill in the art may appreciate the endless possibilities of channel geometries and complex channel configurations that may be integrally formed into the aligner shell. The description of the channel herein is not limiting to any configuration of an integrally formed channel within the aligner shell.

The direct fabrication approaches provided herein are compatible with a wide variety of materials, including but not limited to one or more of the following: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, or combinations thereof. The materials used for direct fabrication can be provided in an uncured form (e.g., as a liquid, resin, powder, etc.) and can be cured (e.g., by photopolymerization, light curing, gas curing, laser curing, crosslinking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate. In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every $n^{th}$ build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

Determination of the appliance geometry, material composition, and/or properties can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, CA For creating finite element models and analyzing them, program products from a number of vendors can be used.

In various embodiments, a computing system can be used in the design of dental appliances thereof that can be used in association with the fabrication of embodiments. Such a computing system may include one or more computing devices having, for example, a processor and memory. The memory can include various types of information including data (e.g., dentition measurement, uploaded images for ornamental designs, and/or digital model data) and/or executable instructions to perform the methods discussed herein. Various embodiments can include one or more input and/or output interfaces. Such interfaces can be used, for instance, to connect the computing device with one or more input or output devices. For example, a system may include connectivity to a scanning device, a camera dock, a keyboard, and/or other peripherals.

Some embodiments can include a network interface. Such an interface can allow, for example, for processing on another networked computing device. Such devices can be used to obtain information about the patient or executable instructions for use with various embodiments provided herein, in some instances. For example, in an embodiment, a patient can select an ornamental design to be integrated with his or her dental appliances. This selection can be made in the patient's home or other location via a network interface. The designs can be uploaded to a website of the dentist, orthodontist, or manufacturer of appliances.

Alternatively, a patient can design a customized image and upload the image to the dentist, orthodontist, or manufacturer via a network interface. In some embodiments, the image is first scanned and then uploaded. The uploaded image(s) can be integrated into the patient's appliance or series of appliances. As noted above, the design can be completely customizable.

Such connectivity can allow for the input of image information (e.g., scanned images and/or digital pictures, etc.), and instructions (e.g., input via keyboard), among other types of information. Although some embodiments may be distributed among various computing devices within one or more networks, such systems can be beneficial in allowing for the capture, calculation, and/or analysis of the various information discussed herein.

Figure 8:
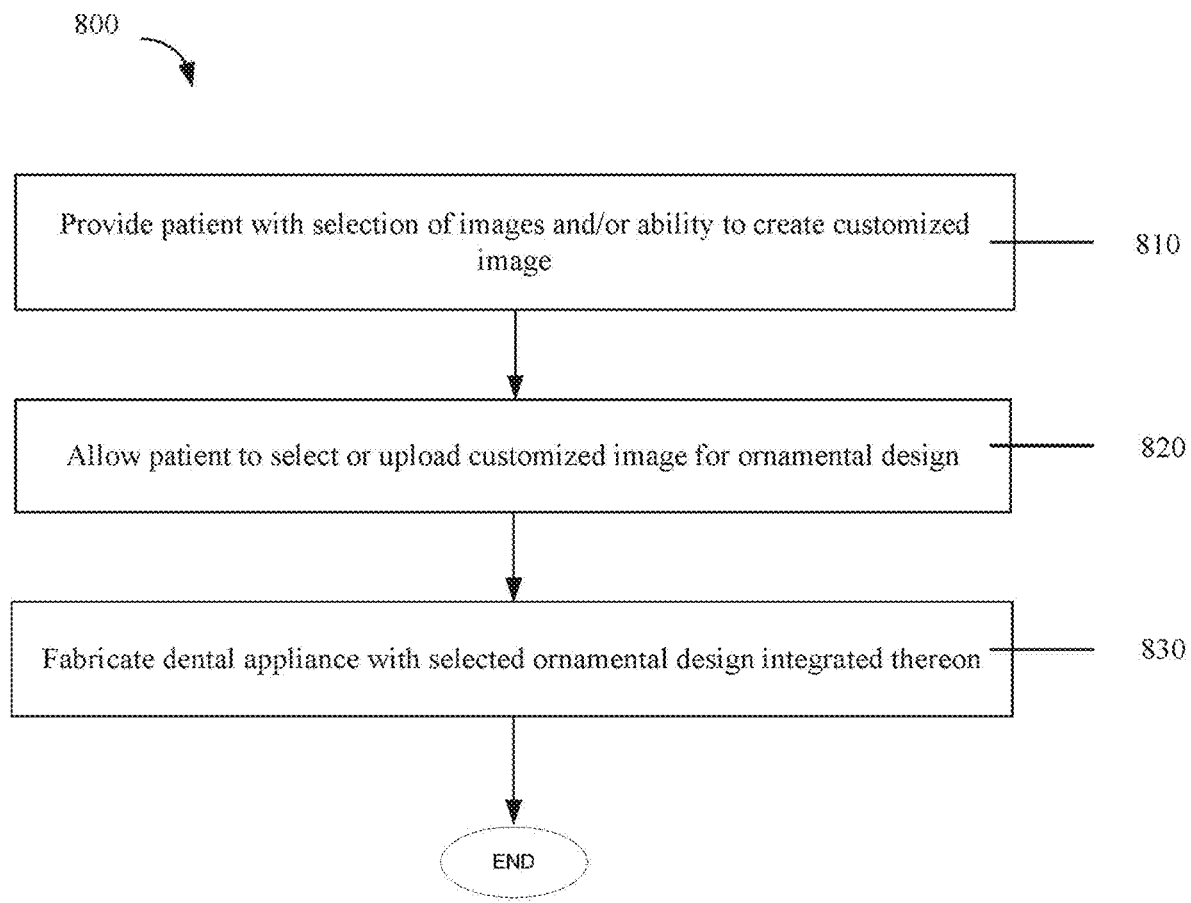
FIG. 8 is a flow chart of a process for fabricating a dental appliance in accordance with another embodiment.

FIG. 8 is a flow chart of a process 800 for selecting an image for integration with a dental appliance. In step 810, the patient is provided with a selection of images and/or the ability to create a customized image for use as an ornamental design integrated with the dental appliance. A website associated with a dentist or orthodontist or a manufacturer of dental appliances can be used to provide the selection of images and/or the ability to create the customized image. The patient can then select the image or upload a customized image from the patient's computer to the web site via a network for use as the ornamental design in step 820. As noted above, a customized image can be created on a computer and then uploaded to the website or the customized image can be scanned using a scanner and uploaded to the website. Alternatively, the customized image can be created directly on the website. The image is then stored on a server associated with the website. The dental appliance can then be fabricated with the selected ornamental design integrated thereon in step 830 by obtaining the selected design from the server. As noted above, there are a variety of methods for fabricating the dental appliances described herein. Digital design can identify where to build up appliance thickness to accommodate the desired design. For example, the thickness of the appliance is known for pre-fabricated design. However, for laser-activated or etched design, a thicker layer may be needed in certain areas. Added thickness can be created by additional colored layers, or spray, painted, or dipped layers. To create a smooth transition, additional thickness can be provided at locations in recessed portions to receive material printed with the ornamental designs.

As discussed above, an appliance for intra-oral delivery of one or more agents to a patient is described herein. The appliance includes a shell forming a plurality of cavities shaped to receive teeth of a mouth of the patient and a reservoir. The reservoir is integrally formed within the shell, and the reservoir is configured to receive, store and release an agent to the patient. A channel can be integrally formed within the shell. The shell and the reservoir can comprise a first material. According to another embodiment, the shell comprises a first material and the reservoir comprises a second material. In yet another embodiment, the reservoir comprises a first material and a second material. In some embodiments, the reservoir is hollow or can be filled with a porous material. The porous material can comprise the second material or a third material. The porous material can be a degradable material or a material configured to release an agent by diffusion. The porous material can have pores having a diameter of about 50 µm, about 30 µm, about 20 µm, about 15 µm, about 10 µm, about 5 µm, about 1 µm, about 500 nm, about 100 nm, about 10 nm, or about 1 nm. The porous material can comprise pores having the same diameter or having different diameters. The reservoir can comprise at least one port, wherein the at least one port is an outlet port, an inlet port or a universal port.

According to another embodiment, a method is described for fabricating an appliance for intra-oral delivery of one or more agents to a patient. A digital model of the appliance is generated. The digital model comprises a digital representation of a shell comprising a plurality of teeth receiving cavities and a digital representation of a reservoir integrally formed within the shell. Instructions are then generated for fabricating the appliance with the shell and integrally formed reservoir using a direct fabrication technique, based on the digital model. The direct fabrication technique can be one or more of: stereolithography, selective laser sintering, fused deposition modeling, or 3D printing The instructions can be configured to control a fabrication machine to form the reservoir concurrently with the shell.

Although only a few embodiments of the invention have been described in detail, it should be appreciated that the invention may be implemented in many other forms without departing from the spirit or scope of the invention. In view of all of the foregoing, it should be apparent that the present embodiments are illustrative and not restrictive and the invention is not limited to the details given herein, but may be modified within the scope and equivalents of the appended claims.

What is claimed is:

1. An appliance for intraoral delivery of an agent, the appliance comprising:
   a shell comprising an inner surface and an outer surface, wherein the inner surface defines a plurality of tooth-receiving cavities configured to apply a repositioning force to a patient's teeth, and the outer surface is oriented away from the patient's teeth;
   a reservoir integrally formed in the outer surface of the shell, wherein the reservoir is configured to store at least one agent; and
   a membrane covering at least a portion of the reservoir to control release of the at least one agent into an intraoral cavity of the patient, wherein the membrane comprises a plurality of pores that are configured to open based at least in part on a temperature of the patient's intraoral cavity to allow the at least one agent to pass therethrough.

2. The appliance of claim 1, wherein the at least one agent comprises one or more of the following: a pharmaceutical composition, a chemical, a gene, a polypeptide, an enzyme, a biomarker, a dye, a compliance indicator, an antibiotic, an analgesic, a medical grade drug, a chemical agent, a bioactive agent, an antibacterial, an antibiotic, an anti-inflammatory agent, an immune-suppressive agent, an immune-stimulatory agent, a dentinal desensitizer, an odor masking agent, an immune reagent, an anesthetic, a nutritional agent, an antioxidant, a lipopolysaccharide complexing agent, or a peroxide.

3. The appliance of claim 1, wherein the appliance is an aligner.

4. The appliance of claim 1, wherein the plurality of tooth-receiving cavities are configured to reposition the patient's teeth from a first arrangement toward a second arrangement.

5. The appliance of claim 1, wherein the reservoir is positioned away from a portion of the shell that is configured to apply the repositioning force to the patient's teeth.

6. The appliance of claim 1, further comprising a port integrally formed in the shell and fluidly coupled to the reservoir.

7. The appliance of claim 1, wherein the reservoir corresponds to at least a portion of an ornamental design formed in the shell, and the at least one agent comprises a colored material corresponding to a color for the ornamental design.

8. The appliance of claim 7, wherein release of the colored material from the reservoir causes fading of the color of the ornamental design, and wherein the membrane is configured to control the release of the colored material such that the fading correlates to compliance with a treatment plan.

9. The appliance of claim 1, wherein the shell comprises a first material, and the membrane comprises a second material different from the first material.

10. The appliance of claim 1, wherein the shell comprises a plurality of cross-sections built up via an additive manufacturing process.

* * * * *